US012115166B2

(12) United States Patent
Howerton et al.

(10) Patent No.: US 12,115,166 B2
(45) Date of Patent: *Oct. 15, 2024

(54) CORTICOTROPIN RELEASING FACTOR RECEPTOR ANTAGONISTS

(71) Applicant: Spruce Biosciences, Inc., South San Francisco, CA (US)

(72) Inventors: Alexis Howerton, South San Francisco, CA (US); Hal Gerber, South San Francisco, CA (US); Michael Huang, South San Francisco, CA (US)

(73) Assignee: SPRUCE BIOSCIENCES, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,718

(22) Filed: Apr. 26, 2023

(65) Prior Publication Data

US 2023/0414627 A1 Dec. 28, 2023

Related U.S. Application Data

(60) Continuation of application No. 18/078,649, filed on Dec. 9, 2022, which is a continuation of application No. 17/586,228, filed on Jan. 27, 2022, now abandoned, which is a division of application No. 17/359,411, filed on Jun. 25, 2021, now Pat. No. 11,351,177, which is a continuation of application No. 17/063,592, filed on Oct. 5, 2020, now Pat. No. 11,344,557, which is a continuation of application No. 16/388,620, filed on Apr. 18, 2019, now Pat. No. 10,849,908, which is a continuation of application No. PCT/US2018/046760, filed on Aug. 14, 2018.

(60) Provisional application No. 62/545,406, filed on Aug. 14, 2017.

(51) Int. Cl.

| A61K 31/5377 | (2006.01) |
| A61K 9/14 | (2006.01) |
| A61K 9/48 | (2006.01) |
| A61K 31/573 | (2006.01) |
| A61P 5/00 | (2006.01) |
| A61P 5/24 | (2006.01) |
| A61P 5/38 | (2006.01) |
| C07D 487/04 | (2006.01) |

(52) U.S. Cl.
CPC ............ *A61K 31/5377* (2013.01); *A61K 9/14* (2013.01); *A61K 9/48* (2013.01); *A61K 9/4825* (2013.01); *A61K 31/573* (2013.01); *A61P 5/00* (2018.01); *A61P 5/24* (2018.01); *A61P 5/38* (2018.01); *C07D 487/04* (2013.01)

(58) Field of Classification Search
None
See application file for complete search history.

(56) References Cited

U.S. PATENT DOCUMENTS

| 8,030,304 | B2 * | 10/2011 | Chen | ...................... A61P 13/12 |
| | | | | 514/366 |
| 8,563,718 | B2 | 10/2013 | Rizzo et al. | |
| 10,849,908 | B2 | 12/2020 | Howerton et al. | |
| 11,007,201 | B2 | 5/2021 | Howerton et al. | |
| 11,311,549 | B2 | 4/2022 | Howerton et al. | |
| 11,344,557 | B2 | 5/2022 | Howerton et al. | |
| 11,351,177 | B2 | 6/2022 | Howerton et al. | |
| 11,708,372 | B2 | 7/2023 | Reddy et al. | |
| 2002/0013357 | A1 | 1/2002 | Nadkarni et al. | |
| 2003/0008885 | A1 | 1/2003 | He et al. | |
| 2005/0209250 | A1 | 9/2005 | Romano | |
| 2006/0078623 | A1 | 4/2006 | Dhoot et al. | |
| 2009/0076266 | A1 | 3/2009 | Daugulis et al. | |
| 2010/0022560 | A1 | 1/2010 | Chen et al. | |
| 2010/0155595 | A1 | 6/2010 | Ghoshal et al. | |
| 2011/0136865 | A1 | 6/2011 | Buntinx | |
| 2013/0045979 | A1 | 2/2013 | Sanfilippo | |
| 2017/0020877 | A1 * | 1/2017 | Grigoriadis | .......... A61K 31/519 |
| 2017/0333126 | A1 | 11/2017 | Sobotka | |
| 2018/0110554 | A1 | 4/2018 | Zarins et al. | |
| 2020/0255436 | A1 | 8/2020 | Howerton et al. | |
| 2021/0015827 | A1 | 1/2021 | Howerton et al. | |
| 2021/0038604 | A1 | 2/2021 | Howerton et al. | |
| 2021/0137935 | A1 | 5/2021 | Howerton et al. | |
| 2021/0322430 | A1 | 10/2021 | Howerton et al. | |
| 2021/0361664 | A1 | 11/2021 | Howerton et al. | |
| 2022/0133742 | A1 | 5/2022 | Ghosh et al. | |
| 2022/0143037 | A1 | 5/2022 | Howerton et al. | |

FOREIGN PATENT DOCUMENTS

| CN | 101516835 A | 8/2009 |
| EP | 2094709 B1 | 9/2010 |
| EP | 3784233 A1 | 3/2021 |
| EP | 3984523 A1 | 4/2022 |
| JP | 2000503661 A | 3/2000 |

(Continued)

OTHER PUBLICATIONS

Speiser et al (J Clin Endocrinol Metabol, 2010, 95(9), 4133-4160 (Year: 2010).*
Trapp et al (Curr Opin Endocrinol Diabetes Obes, Jun. 2011, 18(3), 166-170). (Year: 2011).*
Nella et al (J Clin Endocrinol Metab, Dec. 2016, 101(12), 4690-4698). (Year: 2016).*
EP20844541.1 Extended European Search Report dated May 31, 2023.

(Continued)

*Primary Examiner* — Celeste A Roney
(74) *Attorney, Agent, or Firm* — WILSON SONSINI GOODRICH & ROSATI

(57) ABSTRACT

The present invention provides novel pharmaceutical compositions comprising -(4-Chloro-2-(morpholin-4-yl)thiazol-5-yl)-7-(1-ethylpropyl)-2,5-dimethylpyrazolo(1,5-a)pyrimidine and methods of using the same for the treatment of Congenital adrenal hyperplasia (CAH).

21 Claims, 3 Drawing Sheets

(56) References Cited

FOREIGN PATENT DOCUMENTS

| | | |
|---|---|---|
| JP | 2000302693 A | 10/2000 |
| JP | 2002501922 A | 1/2002 |
| JP | 2002513382 A | 5/2002 |
| JP | 2008533201 A | 8/2008 |
| JP | 2010504344 A | 2/2010 |
| JP | 2012504626 A | 2/2012 |
| JP | 2017503030 A | 1/2017 |
| KR | 20090052366 A | 5/2009 |
| WO | WO-9413676 A1 | 6/1994 |
| WO | WO-9729109 A1 | 8/1997 |
| WO | WO-9803510 A1 | 1/1998 |
| WO | WO-9808847 A1 | 3/1998 |
| WO | WO-0059908 A2 | 10/2000 |
| WO | WO-0123388 A2 | 4/2001 |
| WO | WO-02072202 A1 | 9/2002 |
| WO | WO-2005020910 A2 | 3/2005 |
| WO | WO-2005063755 A1 | 7/2005 |
| WO | WO-2005079868 A2 | 9/2005 |
| WO | WO-2006102194 A1 | 9/2006 |
| WO | WO-2008036579 A1 | 3/2008 |
| WO | WO-2010039678 A1 | 4/2010 |
| WO | WO-2013160317 A2 | 10/2013 |
| WO | WO-2015112642 A1 | 7/2015 |
| WO | WO-2019036472 A1 | 2/2019 |
| WO | WO-2019036503 A1 | 2/2019 |
| WO | WO-2021016208 A1 | 1/2021 |
| WO | WO-2022036123 A1 | 2/2022 |
| WO | WO-2023091684 A1 | 5/2023 |

OTHER PUBLICATIONS

Sarafoglou et al. SUN-LB064 A Phase 2, Dose-Escalation, Safety and Efficacy Study of Tildacerfont (SPR001) for the Treatment of Patients with Classic Congenital Adrenal Hyperplasia. Journal of the Endocrine Society. 2017. vol. 3, Supplement No. 1.
Spruce Biosciences, Inc. Study of SPR001 in Adults with Classic Congenital Adrenal Hyperplasia. 2017. pp. 1-7.
Spruce Biosciences, Inc. Study to Evaluate the Safety and Efficacy of SPR001 in Subjects with Classic Congenital Adrenal Hyperplasia. 2018. pp. 1-7.
U.S. Appl. No. 16/639,540 Office Action dated May 25, 2023.
Bornstein et al. Diagnosis and Treatment of Primary Adrenal Insufficiency: An Endocrine Society Clinical Practice Guideline. J Clin Endocrinol Metab 101(2):364-389 (2016).
Chen et al. Design of 2,5-Dimethyl-3-(6-dimethyl-4-methylpyridin-3-yl)-7-dipropylaminopryazolo[1,5-a]pyrimidine (NBI 30775/R121919) and Structure-Activity Relationships of a Series of Potent and Orally Active Corticotropin-Releasing Factor Receptor Antagonists. J. O Medicinal Chemistry Society 47(19) 4787-4798 XP001206057 (2004).
Co-pending U.S. Appl. No. 17/720,074, inventors Reddy; Dasharatha et al., filed Apr. 13, 2022.
Co-pending U.S. Appl. No. 18/078,649, inventors Howerton; Alexis et al., filed Dec. 9, 2022.
Co-pending U.S. Appl. No. 18/310,463, inventor Reddy; Dasharatha, filed May 1, 2023.
Dave. Overview of pharmaceutical excipients used in tablets and capsules. https://www.drugtopics.com/view/overview-pharmaceutical-excipients-used-tablets-and-capsules (Oct. 24, 2008).
EP18846043.0 Extended Search Report dated Feb. 10, 2021.
EP18846689.0 Extended European Search Report dated Dec. 22, 2020.
Escobar-Morreale, HF., Polycystic ovary syndrome: definition, aetiology, diagnosis and treatment. Nat Rev Endocrinol. 14(5):270-284 (2018).
Fuqua et al. Duration of suppression of adrenal steroids after glucocorticoid administration. Int J Pediatr Endocrinol 2010:712549 (2010).
Gehlert et al. 3-(4-Chloro-2-morpholin-4-yl-thiazol-5-yl )-8-(1-ethylpropy1)-2,6-dimethyl-imidazo[1,2-b]pyridazine: a novel brain-penetrant, orally available corticotropin-releasing factor receptor 1 antagonist with efficacy in animal models of alcoholism. The Journal of Neuroscience 27(10):2718-2726 (2007).
Gennaro. Remington: The Science and Practice of Pharmacy. 21st Ed. Mack Pub. Co., Easton, PA (2005).
Gilligan P. et al., The Discovery of 4-(3-Pentylamino)-2,7-dimethyl-8-(2-methyl-4-methoxyphenyl)-pyrazolo-[1,5-alpha]-pyrimidine: A corticotrophin-Releasing Factor (hCRF1)Antagonist. Bioorganic & Medicinal Chemistry 181-189 (2000).
He Liqi et al. 4-(1,3-Dimethoxyprop-2-ylamino)-2,7-dimethyl-8-(2,4-dichlorophenyl)pyrazolo[1,5-a]-1,3,5-triazine: A Potent, Orally Bioavailable CRF1 Receptor Antagonist. J. of Medicinal Chem. American Chem. Society. Washington, US, vol. 43, 449-456 XP002196777 (2000).
Hien-Quang Do. A General Method for Copper-Catalyzed Arylation of Arene C-H Bonds. J Am Chem Soc. Nov. 12, 2008; 130(45): 15185-15192.
Hien-Quang Do. Copper-Catalyzed Arylation and Alkenylation of Polyfluoroarene C-H Bonds. Journal of American Chemical Society 2008, 1128-1129.
Hien-Quang Do. Copper-Catalyzed Arylation of Heterocycle C-H Bonds. J Am Chem Soc. Oct. 17, 2007; 129(41): 12404-12405.
Hodgetts et al. Discovery of N-(1-ethylpropyl)-[3-methoxy-5-(2-methoxy-4-trifluoromethoxyphenyl)-6-methyl-pyrazin-2-yl]amine 59 (NGD 98-2): an orally active corticotropin releasing factor-1 (CRF-1) receptor antagonist. J Med Chem 54:4187-4206 (2011).
Khadilkar et al., Can polycystic ovarian syndrome be cured? Unfolding the concept of secondary polycystic ovarian syndrome. J Obstet Gynaecol India 69(4):297-302 (2019).
Lee et al. Attenuated Forms of Congenital Adrenal Hyperplasia due to 21-Hydroxylase Deficiency. J Clin Endocrinol Metab. 55(5):866-871 (1982).
Majo et al. Facile Palladium-Catalyzed Synthesis of 3-Arylpyrazolo-[1,5-a]pyrimidines. Adv. Synth. Catal. 2003, 620-624.
Malvern Instruments Worldwide. A Basic Guide to Particle Characterization. Inform—White Paper. 2012. 26 Pages.
O'Reilly et al., 11-oxygenated C19 steroids are the predominant androgens in polycystic ovary syndrome. J Clin Endocrinol Metab. 102(3):840-848 (2017).
PCT/US2007/078605 Written Opinion dated Mar. 20, 2009.
PCT/US2009/058722 International Search Report dated Apr. 8, 2010.
PCT/US2009/058722 Written Opinion dated Apr. 2, 2011.
PCT/US2018/046707 International Search Report and Written Opinion dated Oct. 24, 2018.
PCT/US2018/046760 International Search Report and Written Opinion dated Oct. 24, 2018.
PCT/US2020/042820 International Search Report and Written Opinion dated Nov. 25, 2020.
PCT/US2021/045780 International Search Report and Written Opinion dated Dec. 17, 2021.
PCT/US2022/050436 International Search Report and Written Opinion dated Nov. 18, 2022.
Rosenfield et al., The pathogenesis of polycystic ovary syndrome (PCOS): the hypothesis of PCOS as functional ovarian hyperandrogenism revisited. Endocrine Reviews 37(5):467-520 (2016).
Sarafoglou et al. Tildacerfont in Adults with Classic Congenital Adrenal Hyperplasia: Results from Two Phase 2 Studies. J Clin Endocrinol Metab. Oct. 21, 2021; 106(11):e4666-e4679.
Thakral et al. Salt Disproportionation in the Solid State: Role of Solubility and Counterion Volatility. Mol Pharm 13(12):4141-4151 (2016).
Turcu et al. Single-Dose Study of a Corticotripin-Releasing Factor Receptor-1 Antagonist in Women With 21-Hydroxylase Deficiency. J Clin Endocrinol Metab 101(3):1174-1180 (2016).
U.S. Appl. No. 16/388,620 Notice of Allowance dated Sep. 30, 2020.
U.S. Appl. No. 17/063,592 Notice of Allowance dated Mar. 25, 2022.
U.S. Appl. No. 17/078,054 Notice of Allowance dated Mar. 9, 2021.
U.S. Appl. No. 17/359,414 Notice of Allowance dated Mar. 4, 2022.
U.S. Appl. No. 17/586,228 Office Action dated Jun. 10, 2022.

(56) References Cited

OTHER PUBLICATIONS

U.S. Appl. No. 12/377,733 Notice of Allowance dated May 27, 2011.
U.S. Appl. No. 16/388,620 Office Action dated Jul. 15, 2019.
U.S. Appl. No. 16/388,620 Office Action dated Nov. 25, 2019.
U.S. Appl. No. 16/639,540 Office Action dated Jul. 11, 2022.
U.S. Appl. No. 16/639,540 Office Action dated Nov. 16, 2021.
U.S. Appl. No. 17/063,592 Office Action dated Dec. 7, 2021.
U.S. Appl. No. 17/078,054 Office Action dated Dec. 14, 2020.
U.S. Appl. No. 17/359,411 Notice of Allowance dated Apr. 28, 2022.
U.S. Appl. No. 17/359,411 Notice of Allowance dated Apr. 4, 2022.
U.S. Appl. No. 17/359,411 Notice of Allowance dated Mar. 22, 2022.
U.S. Appl. No. 17/359,411 Office Action dated Jan. 6, 2022.
U.S. Appl. No. 17/359,414 Office Action dated Nov. 16, 2021.
U.S. Appl. No. 17/720,074 Notice of Allowance dated Mar. 28, 2023.
U.S. Appl. No. 17/720,074 Office Action dated Aug. 26, 2022.
Varma. Excipients used in the Formulation of Tablets. https://www.rroij.com/openaccess/excipients-used-in-the-formulationof-tablets-.php?aid=78260 Revised date: Jul. 26, 2016.
Zhang et al. D-Level Essay in Statistics, 2009, How to Analyze Change from Baseline. Available at http://www.statistics.du.se/essays/D09 Zhang%20Ling%20&%20Han%20Kun.pdf (Jun. 10, 2009).
U.S. Pat. No. 10,849,908—*Neurocrine Biosciences, Inc.* (Petitioner) v. *Spruce Biosciences, Inc.* (Patent Owner). Decision Granting Institution of Post-Grant Review dated Dec. 1, 2023. 57 pages.
Abcam. CP 154526 hydrochloride, non-peptide CRF1 receptor antagonist ab141429. Product datasheet. Retrieved online on Sep. 19, 2023 at: https://www.abcam.com/products/biochemicals/cp-154526-hydrochloride-non-peptide-crf1-receptor-antagonist-ab141429.html. 2 pages.
Chen, C. Recent Advances in Small Molecule Antagonists of the Corticotropin-Releasing Factor Type-1 Receptor-Focus on Pharmacology and Pharmacokinetics. Current Medicinal Chemistry, 2006, 13, 1261-1282.
Million et al. A novel water-soluble selective CRF1 receptor antagonist, NBI 35965, blunts stress-induced visceral hyperalgesia and colonic motor function in rats. Brain Research, vol. 985, Issue 1, 2003, pp. 32-42.
Morabbi et al. Pexacerfont as a CRF1 antagonist for the treatment of withdrawal symptoms in men with heroin/methamphetamine dependence: a randomized, double-blind, placebo-controlled clinical trial. International Clinical Psychopharmacology 2017, vol. 00, No. 00. 9 pages.
U.S. Appl. No. 16/639,540 Office Action dated Sep. 28, 2023.
U.S. Appl. No. 18/078,649 Office Action dated Sep. 8, 2023.
Zorrilla et al. Progress in corticotropin-releasing factor-1 antagonist development. NIH Public Access—Author Manuscript provided (2011). 24 pages. Published in final edited form as: Drug Discov Today 2010; 15(9-10): 371-383.
U.S. Appl. No. 16/639,540 Office Action dated Mar. 28, 2024.
U.S. Appl. No. 18/078,649 Office Action dated Mar. 21, 2024.
Do, Hien-Quang et. al; Copper-catalyzed arylation of C-H bonds; Abstracts of Papers, 236th ACS National Meeting, New Orleans, LA, Apr. 6-10, 2008, Accession No. 2008:390596.
*Neurocrine Biosciences, Inc.* (Petitioner) v. *Spruce Biosciences, Inc.* (Patent Owner). Decision Granting Institution of Post-Grant Review of U.S. Pat. No. 11,007,201 dated Dec. 1, 2023 (pp. 1-38).
*Neurocrine Biosciences, Inc.* (Petitioner) v. *Spruce Biosciences, Inc.* (Patent Owner). Petition for Post-Grant Review of U.S. Pat. No. 10,849,908 dated May 28, 2021 (pp. 1-92).
*Neurocrine Biosciences, Inc.* (Petitioner) v. *Spruce Biosciences, Inc.* (Patent Owner). Petition for Post-Grant Review of U.S. Pat. No. 11,007,201 dated Feb. 18, 2022 (pp. 1-92).
U.S. Appl. No. 16/639,541 Office Action dated Apr. 4, 2022.
U.S. Appl. No. 17/586,228 Office Action dated Mar. 30, 2022.

\* cited by examiner

CORTICOTROPIN RELEASING FACTOR RECEPTOR ANTAGONISTS

CROSS-REFERENCE

This patent application is a continuation of U.S. patent application Ser. No. 18/078,649, filed Dec. 9, 2022; which is a continuation of U.S. patent application Ser. No. 17/586,228, filed Jan. 27, 2022; which is a divisional of U.S. patent application Ser. No. 17/359,411, filed on Jun. 25, 2021, now U.S. Pat. No. 11,351,177; which is a continuation of U.S. patent application Ser. No. 17/063,592, filed on Oct. 5, 2020, now U.S. Pat. No. 11,344,557; which is a continuation of U.S. patent application Ser. No. 16/388,620, filed on Apr. 18, 2019, now U.S. Pat. No. 10,849,908; which is a continuation of PCT Application No. PCT/US2018/046760, filed on Aug. 14, 2018; which claims the benefit of U.S. Provisional Patent Application No. 62/545,406, filed Aug. 14, 2017; all of which are incorporated herein by reference in their entirety.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in the brain. There is also evidence that CRF plays a significant role in integrating the response in the immune system to physiological, psychological, and immunological stressors.

SUMMARY OF THE INVENTION

The present invention provides novel pharmaceutical compositions comprising 3-(4-Chloro-2-(morpholin-4-yl)thiazol-5-yl)-7-(1-ethylpropyl)-2,5-dimethylpyrazolo(1,5-a)pyrimidine and methods using such pharmaceutical compositions for treating congenital adrenal hyperplasia (CAH).

In one aspect, the present disclosure provides a method of treating congenital adrenal hyperplasia (CAH) in a subject in need thereof, comprising administering a pharmaceutical composition comprising Compound 1:

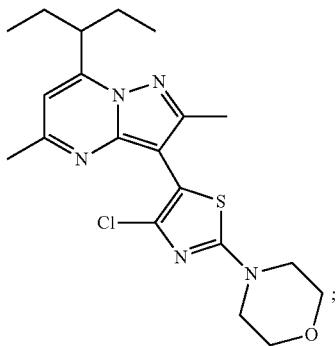 [SMILES: CCC(CC)c1cc(C)nc2c(-c3sc(N4CCOCC4)nc3Cl)c(C)nn12]

or a pharmaceutically acceptable salt or solvate thereof, wherein Compound 1 is administered at a dose between about 50 mg/day and about 1600 mg/day.

In some embodiments, Compound 1, or a pharmaceutically acceptable salt or solvate thereof, is administered at a dose between about 50 mg/day and about 1200 mg/day. In some embodiments, Compound 1, or a pharmaceutically acceptable salt or solvate thereof, is administered at a dose between about 50 mg/day and about 1000 mg/day. In some embodiments, Compound 1, or a pharmaceutically acceptable salt or solvate thereof, is administered at a dose between about 50 mg/day and about 800 mg/day. In some embodiments, Compound 1, or a pharmaceutically acceptable salt or solvate thereof, is administered at a dose between about 100 mg/day and about 600 mg/day. In some embodiments, Compound 1, or a pharmaceutically acceptable salt or solvate thereof, is administered at a dose between about 200 mg/day and 400 mg/day. In some embodiments, Compound 1, or a pharmaceutically acceptable salt or solvate thereof, is administered at a dose of about 200 mg/day.

In some embodiments, Compound 1, or a pharmaceutically acceptable salt or solvate thereof, is in the form of microparticles. In some embodiments, the average size of the microparticles is between about 1 μm and about 20 μm. In some embodiments, the average size of the microparticles is between about 5 μm and about 15 μm. In some embodiments, the average size of the microparticles is less than about 10 μm.

In some embodiments, the pharmaceutical composition is in the form of a capsule or a tablet. In some embodiments, the pharmaceutical composition is in the form of a capsule. In some embodiments, the capsule is a hard gelatin capsule. In some embodiments, the capsule is a soft gelatin capsule. In some embodiments, the capsule is formed using materials selected from the group consisting of natural gelatin, synthetic gelatin, pectin, casein, collagen, protein, modified starch, polyvinylpyrrolidone, acrylic polymers, cellulose derivatives, and any combinations thereof.

In some embodiments, the pharmaceutical composition is free of additional excipients. In some embodiments, the pharmaceutical composition further comprises one or more pharmaceutically acceptable excipients.

In some embodiments, the pharmaceutical composition is in the form of a tablet. In some embodiments, the pharmaceutical composition further comprises one or more pharmaceutically acceptable excipients. In some embodiments, the pharmaceutical composition comprises between about 1 mg and about 500 mg of Compound 1, or a pharmaceutically acceptable salt or solvate thereof. In some embodiments, the pharmaceutical composition comprises between about 5 mg and about 500 mg of Compound 1, or a pharmaceutically acceptable salt or solvate thereof. In some embodiments, the pharmaceutical composition comprises between about 10 mg and about 500 mg of Compound 1, or a pharmaceutically acceptable salt or solvate thereof. In some embodiments, the pharmaceutical composition comprises between about 10 mg and about 300 mg of Compound 1, or a pharmaceutically acceptable salt or solvate thereof. In some embodiments, the pharmaceutical composition comprises between about 10 mg and about 100 mg of Compound 1, or a pharmaceutically acceptable salt or solvate thereof. In some embodiments, the pharmaceutical composition comprises between about 50 mg and about 500 mg of Compound 1, or a pharmaceutically acceptable salt or solvate thereof. In some embodiments, the pharmaceutical composition comprises between about 100 mg and about 400 mg of Compound 1, or a pharmaceutically acceptable salt or solvate thereof. In some embodiments, the pharmaceutical composition comprises between about 100 mg and about 300 mg of Compound 1, or a pharmaceutically acceptable salt or solvate thereof. In some embodiments, the pharmaceutical composition comprises between about 150 mg and about 250 mg of Compound 1, or a pharmaceutically acceptable salt or solvate thereof.

In some embodiments, the pharmaceutical composition comprises about 400 mg of Compound 1, or a pharmaceutically acceptable salt or solvate thereof. In some embodiments, the pharmaceutical composition comprises about 300 mg of Compound 1, or a pharmaceutically acceptable salt or solvate thereof. In some embodiments, the pharmaceutical composition comprises about 250 mg of Compound 1, or a pharmaceutically acceptable salt or solvate thereof. In some embodiments, the pharmaceutical composition comprises about 200 mg of Compound 1, or a pharmaceutically acceptable salt or solvate thereof. In some embodiments, the pharmaceutical composition comprises about 150 mg of Compound 1, or a pharmaceutically acceptable salt or solvate thereof. In some embodiments, the pharmaceutical composition comprises about 100 mg of Compound 1, or a pharmaceutically acceptable salt or solvate thereof. In some embodiments, the pharmaceutical composition comprises about 80 mg of Compound 1, or a pharmaceutically acceptable salt or solvate thereof. In some embodiments, the pharmaceutical composition comprises about 60 mg of Compound 1, or a pharmaceutically acceptable salt or solvate thereof. In some embodiments, the pharmaceutical composition comprises about 50 mg of Compound 1, or a pharmaceutically acceptable salt or solvate thereof. In some embodiments, the pharmaceutical composition comprises about 30 mg of Compound 1, or a pharmaceutically acceptable salt or solvate thereof.

In some embodiments, the pharmaceutical composition provides a Compound 1 $T_{max}$ of about 2 to about 6 hours in a subject. In some embodiments, the pharmaceutical composition provides a Compound 1 $T_{max}$ of about 3 to about 5 hours in a subject. In some embodiments, the pharmaceutical composition provides a Compound 1 $T_{max}$ of about 6 hours in a subject. In some embodiments, the pharmaceutical composition provides a Compound 1 $T_{max}$ of about 5 hours in a subject. In some embodiments, the pharmaceutical composition provides a Compound 1 $T_{max}$ of about 4 hours in a subject. In some embodiments, the pharmaceutical composition provides a Compound 1 $T_{max}$ of about 3 hours in a subject.

In some embodiments, the pharmaceutical composition is administered in the fed state. In some embodiments, the pharmaceutical composition is administered in the fasted state. In some embodiments, the pharmaceutical composition is administered once a day. In some embodiments, the pharmaceutical composition is administered twice a day. In some embodiments, the pharmaceutical composition is administered three times a day.

In some embodiments, the method further comprises administering a glucocorticoid. In some embodiments, the amount of glucocorticoid administered is reduced as compared to a method not comprising administering Compound 1, or a pharmaceutically acceptable salt or solvate thereof. In some embodiments, the amount of glucocorticoid used is reduced from a supraphysiologic amount to a physiologic amount. In some embodiments, the amount of glucocorticoid is reduced by about 5%, about 10%, about 15%, about 20%, about 25%, about 30%, about 35%, about 40%, about 45%, about 50%, about 55%, or about 60%.

In some embodiments, the symptoms associated with high-dose glucocorticoid therapy are reduced. In some embodiments, the symptoms associated with high-dose glucocorticoid therapy are obesity, insulin resistance, metabolic abnormalities, hypertension, cardiovascular diseases, or osteoporosis. In some embodiments, the glucocorticoid is beclomethasone, betamethasone, budesonide, cortisone, dexamethasone, hydrocortisone, methylprednisolone, prednisolone, prednisone, or triamcinolone.

In some embodiments, the glucocorticoid is hydrocortisone. In some embodiments, the hydrocortisone is administered at a dose less than about 15 mg/day. In some embodiments, the hydrocortisone is administered at a dose less than about 10 mg/day. In some embodiments, the hydrocortisone is administered at a dose less than about 5 mg/day.

In some embodiments, Compound 1, or a pharmaceutically acceptable salt or solvate thereof, and the glucocorticoid are administered concurrently. In some embodiments, Compound 1, or a pharmaceutically acceptable salt or solvate thereof, and the glucocorticoid are administered sequentially. In some embodiments, Compound 1, or a pharmaceutically acceptable salt or solvate thereof, and the glucocorticoid are administered sequentially within 24 hours. In some embodiments, Compound 1, or a pharmaceutically acceptable salt or solvate thereof, and the glucocorticoid are administered sequentially within 8 hours. In some embodiments, Compound 1, or a pharmaceutically acceptable salt or solvate thereof, and the glucocorticoid are administered sequentially within 2 hours. In some embodiments, Compound 1, or a pharmaceutically acceptable salt or solvate thereof, and the glucocorticoid are administered sequentially within 30 minutes.

In some embodiments, the method further comprises administering a mineralocorticoid. In some embodiments, the mineralocorticoid is fludrocortisone.

In some embodiments, the pharmaceutical composition is administered at bedtime. In some embodiments, the pharmaceutical composition is administered less than about 4 hours before sleep. In some embodiments, the pharmaceutical composition is administered less than about 2 hours before sleep. In some embodiments, the pharmaceutical composition is administered less than about 30 mins before sleep. In some embodiments, the pharmaceutical composition is administered in the evening. In some embodiments, the pharmaceutical composition is administered at about 10 pm at night. In some embodiments, the pharmaceutical composition is administered at or before the expected circadian release of adrenocorticotropic hormone (ACTH). In some embodiments, the pharmaceutical composition is administered about 3-4 hours before the expected circadian release of adrenocorticotropic hormone (ACTH).

In some embodiments, CAH is classic CAH. In some embodiments, CAH is non-classic CAH.

In one aspect, the present disclosure provides a method of treating congenital adrenal hyperplasia (CAH) in a subject in need thereof, the method comprising: (i) measuring a hormone level in the subject in need thereof; (ii) administering Compound 1:

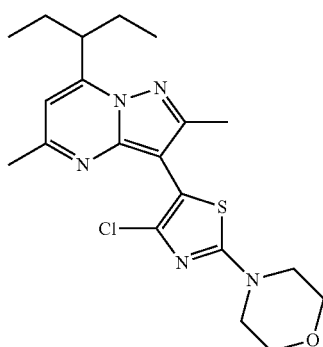

or a pharmaceutically acceptable salt or solvate thereof; and (iii) repeating steps (i) and (ii) until the hormone level reaches a pre-determined range followed by a maintenance therapy of a daily dosing of compound 1.

In some embodiments, the hormone is 17α-Hydroxyprogesterone (17-OHP), adrenocorticotropic hormone (ACTH), testosterone, or androstenedione. In some embodiments, the hormone is 17-OHP, and the pre-determined range is from about 200 ng/dL to about 400 ng/dL. In some embodiments, the hormone is ACTH, and the pre-determined range is below about 100 pg/mL. In some embodiments, the hormone is testosterone and the pre-determined range is from about 14 ng/dL to about 76 ng/dL. In some embodiments, the hormone is androstenedione and the pre-determined range is from about 30 ng/dL to about 150 ng/dL in males. In some embodiments, the hormone is androstenedione and the pre-determined range is from about 40 ng/dL to about 200 ng/dL in females.

In some embodiments, Compound 1, or a pharmaceutically acceptable salt or solvate thereof, is administered at a dose between about 200 mg/day and about 1600 mg/day. In some embodiments, Compound 1, or a pharmaceutically acceptable salt or solvate thereof, is administered at a dose between about 200 mg/day and about 1200 mg/day. In some embodiments, Compound 1, or a pharmaceutically acceptable salt or solvate thereof, is administered at a dose between about 200 mg/day and about 1000 mg/day. In some embodiments, Compound 1, or a pharmaceutically acceptable salt or solvate thereof, is administered at a dose between about 200 mg/day and about 800 mg/day. In some embodiments, Compound 1, or a pharmaceutically acceptable salt or solvate thereof, is administered at a dose between about 200 mg/day and about 600 mg/day. In some embodiments, Compound 1, or a pharmaceutically acceptable salt or solvate thereof, is administered at a dose between about 200 mg/day and 400 mg/day. In some embodiments, Compound 1, or a pharmaceutically acceptable salt or solvate thereof, is administered at a dose of about 200 mg/day.

In some embodiments, Compound 1, or a pharmaceutically acceptable salt or solvate thereof, is administered at a dose between about 50 mg/day and about 1600 mg/day. In some embodiments, Compound 1, or a pharmaceutically acceptable salt or solvate thereof, is administered at a dose between about 50 mg/day and about 1200 mg/day. In some embodiments, Compound 1, or a pharmaceutically acceptable salt or solvate thereof, is administered at a dose between about 50 mg/day and about 1000 mg/day. In some embodiments, Compound 1, or a pharmaceutically acceptable salt or solvate thereof, is administered at a dose between about 50 mg/day and about 800 mg/day. In some embodiments, Compound 1, or a pharmaceutically acceptable salt or solvate thereof, is administered at a dose between about 50 mg/day and about 600 mg/day. In some embodiments, Compound 1, or a pharmaceutically acceptable salt or solvate thereof, is administered at a dose between about 50 mg/day and 400 mg/day. In some embodiments, Compound 1, or a pharmaceutically acceptable salt or solvate thereof, is administered at a dose between 50 mg/day and 200 mg/day. In some embodiments, Compound 1, or a pharmaceutically acceptable salt or solvate thereof, is administered at a dose of about 50 mg/day.

In some embodiments, Compound 1, or a pharmaceutically acceptable salt or solvate thereof, is in the form of microparticles. In some embodiments, the average size of the microparticles is between about 1 μm and about 20 μm. In some embodiments, the average size of the microparticles is between about 5 μm and about 15 μm. In some embodiments, the average size of the microparticles is less than about 10 μm.

In some embodiments, Compound 1 is formulated in a pharmaceutical composition in the form of a capsule or a tablet. In some embodiments, the pharmaceutical composition is in the form of a capsule. In some embodiments, the capsule is a hard gelatin capsule. In some embodiments, the capsule is a soft gelatin capsule. In some embodiments, the capsule is formed using materials selected from the group consisting of natural gelatin, synthetic gelatin, pectin, casein, collagen, protein, modified starch, polyvinylpyrrolidone, acrylic polymers, cellulose derivatives, and any combinations thereof.

In some embodiments, the pharmaceutical composition is free of additional excipients. In some embodiments, the pharmaceutical composition further comprises one or more pharmaceutically acceptable excipients. In some embodiments, the pharmaceutical composition is in the form of a tablet. In some embodiments, the pharmaceutical composition further comprises one or more pharmaceutically acceptable excipients.

In some embodiments, the pharmaceutical composition comprises between about 1 mg and about 500 mg of Compound 1, or a pharmaceutically acceptable salt or solvate thereof. In some embodiments, the pharmaceutical composition comprises between about 5 mg and about 500 mg of Compound 1, or a pharmaceutically acceptable salt or solvate thereof. In some embodiments, the pharmaceutical composition comprises between about 10 mg and about 500 mg of Compound 1, or a pharmaceutically acceptable salt or solvate thereof. In some embodiments, the pharmaceutical composition comprises between about 10 mg and about 300 mg of Compound 1, or a pharmaceutically acceptable salt or solvate thereof. In some embodiments, the pharmaceutical composition comprises between about 10 mg and about 100 mg of Compound 1, or a pharmaceutically acceptable salt or solvate thereof. In some embodiments, the pharmaceutical composition comprises between about 50 mg and about 500 mg of Compound 1, or a pharmaceutically acceptable salt or solvate thereof. In some embodiments, the pharmaceutical composition comprises between about 100 mg and about 400 mg of Compound 1, or a pharmaceutically acceptable salt or solvate thereof. In some embodiments, the pharmaceutical composition comprises between about 100 mg and about 300 mg of Compound 1, or a pharmaceutically acceptable salt or solvate thereof. In some embodiments, the pharmaceutical composition comprises between about 150 mg and about 250 mg of Compound 1, or a pharmaceutically acceptable salt or solvate thereof.

In some embodiments the pharmaceutical composition comprises about 400 mg of Compound 1, or a pharmaceutically acceptable salt or solvate thereof. In some embodiments, the pharmaceutical composition comprises about 300 mg of Compound 1, or a pharmaceutically acceptable salt or solvate thereof. In some embodiments, the pharmaceutical composition comprises about 250 mg of Compound 1, or a pharmaceutically acceptable salt or solvate thereof. In some embodiments, the pharmaceutical composition comprises about 200 mg of Compound 1, or a pharmaceutically acceptable salt or solvate thereof. In some embodiments, the pharmaceutical composition comprises about 150 mg of Compound 1, or a pharmaceutically acceptable salt or solvate thereof. In some embodiments, the pharmaceutical composition comprises about 100 mg of Compound 1, or a pharmaceutically acceptable salt or solvate thereof. In some embodiments, the pharmaceutical composition comprises about 80 mg of Compound 1, or a pharmaceutically acceptable salt or solvate thereof. In some embodiments, the pharmaceutical composition comprises about 60 mg of Compound 1, or a pharmaceutically acceptable salt or solvate thereof. In some embodiments, the pharmaceutical composition comprises about 50 mg of Compound 1, or a pharmaceutically acceptable salt or solvate thereof. In some embodiments, the pharmaceutical composition comprises about 30 mg of Compound 1, or a pharmaceutically acceptable salt or solvate thereof.

In some embodiments, the pharmaceutical composition provides a Compound 1 $T_{max}$ of about 2 to about 6 hours in a subject. In some embodiments, the pharmaceutical composition provides a Compound 1 $T_{max}$ of about 3 to about 5 hours in a subject. In some embodiments, the pharmaceutical composition provides a Compound 1 $T_{max}$ of about 6 hours in a subject. In some embodiments, the pharmaceutical composition provides a Compound 1 $T_{max}$ of about 5 hours in a subject. In some embodiments, the pharmaceutical composition provides a Compound 1 $T_{max}$ of about 4 hours in a subject. In some embodiments, the pharmaceutical composition provides a Compound 1 $T_{max}$ of about 3 hours in a subject.

In some embodiments, the pharmaceutical composition is administered in the fed state. In some embodiments, the pharmaceutical composition is administered in the fasted state. In some embodiments, the pharmaceutical composition is administered once a day. In some embodiments, the pharmaceutical composition is administered twice a day. In some embodiments, the pharmaceutical composition is administered three times a day.

In some embodiments, the method further comprises administering a glucocorticoid. In some embodiments, the amount of glucocorticoid administered is reduced as compared to a method not comprising administering Compound 1, or a pharmaceutically acceptable salt or solvate thereof. In some embodiments, the amount of glucocorticoid used is reduced from a supraphysiologic amount to a physiologic amount. In some embodiments, the amount of glucocorticoid is reduced by about 5%, about 10%, about 15%, about 20%, about 25%, about 30%, about 35%, about 40%, about 45%, about 50%, about 55%, or about 60%.

In some embodiments, the symptoms associated with high-dose glucocorticoid therapy are reduced. In some embodiments, the symptoms associated with high-dose glucocorticoid therapy are obesity, insulin resistance, metabolic abnormalities, hypertension, cardiovascular diseases, or osteoporosis. In some embodiments, the glucocorticoid is beclomethasone, betamethasone, budesonide, cortisone, dexamethasone, hydrocortisone, methylprednisolone, prednisolone, prednisone, or triamcinolone. In some embodiments, the glucocorticoid is hydrocortisone.

In some embodiments, the hydrocortisone is administered at a dose less than about 15 mg/day. In some embodiments, the hydrocortisone is administered at a dose less than about 10 mg/day. In some embodiments, the hydrocortisone is administered at a dose less than about 5 mg/day.

In some embodiments, Compound 1, or a pharmaceutically acceptable salt or solvate thereof, and the glucocorticoid are administered concurrently. In some embodiments, Compound 1, or a pharmaceutically acceptable salt or solvate thereof, and the glucocorticoid are administered sequentially. In some embodiments, Compound 1, or a pharmaceutically acceptable salt or solvate thereof, and the glucocorticoid are administered sequentially within 24 hours. In some embodiments, Compound 1, or a pharmaceutically acceptable salt or solvate thereof, and the glucocorticoid are administered sequentially within 8 hours. In some embodiments, Compound 1, or a pharmaceutically acceptable salt or solvate thereof, and the glucocorticoid are administered sequentially within 2 hours. In some embodiments, Compound 1, or a pharmaceutically acceptable salt or solvate thereof, and the glucocorticoid are administered sequentially within 30 minutes.

In some embodiments, the method further comprises administering a mineralocorticoid. In some embodiments, the mineralocorticoid is fludrocortisone.

In some embodiments, Compound 1, or a pharmaceutically acceptable salt or solvate thereof, is administered at bedtime. In some embodiments, Compound 1, or a pharmaceutically acceptable salt or solvate thereof, is administered less than about 4 hours before sleeping. In some embodiments, Compound 1, or a pharmaceutically acceptable salt or solvate thereof, is administered less than about 2 hours before sleeping. In some embodiments, Compound 1, or a pharmaceutically acceptable salt or solvate thereof, is administered less than about 30 mins before sleeping. In some embodiments, Compound 1, or a pharmaceutically acceptable salt or solvate thereof, is administered in the evening. In some embodiments, Compound 1, or a pharmaceutically acceptable salt or solvate thereof, is administered at 10 pm at night.

In some embodiments, Compound 1, or a pharmaceutically acceptable salt or solvate thereof, is administered at or before the expected circadian release of adrenocorticotropic hormone (ACTH). In some embodiments, Compound 1, or a pharmaceutically acceptable salt or solvate thereof, is administered about 3-4 hours before the expected circadian release of adrenocorticotropic hormone (ACTH).

In some embodiments, CAH is classic CAH. In some embodiments, CAH is non-classic CAH.

In some embodiments, the subject in need thereof is from about 12 years of age to about 20 years of age.

In one aspect, the present disclosure provides a method of improving hyperandrogenic symptoms in a subject in need thereof, comprising administering a pharmaceutical composition comprising Compound 1:

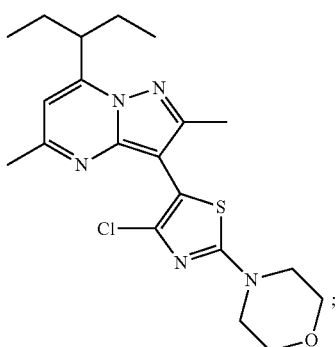

or a pharmaceutically acceptable salt or solvate thereof, wherein Compound 1 is administered at a dose between about 50 mg/day and about 1600 mg/day. In some embodiments, the hyperandrogenic symptoms are selected from the group consisting of acne, hirsutism and alopecia.

In one aspect, the present disclosure provides a method of treating menstrual irregularity, ovulatory dysfunction or infertility, in a subject in need thereof, comprising administering a pharmaceutical composition comprising Compound 1:

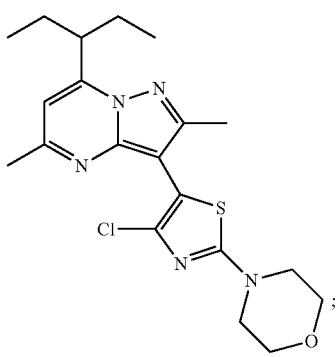 [SMILES: CCC(CC)c1cc(C)nc2c(-c3sc(N4CCOCC4)nc3Cl)c(C)nn12]

or a pharmaceutically acceptable salt or solvate thereof, wherein Compound 1 is administered at a dose between about 50 mg/day and about 1600 mg/day.

In one aspect, the present disclosure provides a method of improving metabolic symptoms in a subject in need thereof, comprising administering a pharmaceutical composition comprising Compound 1:

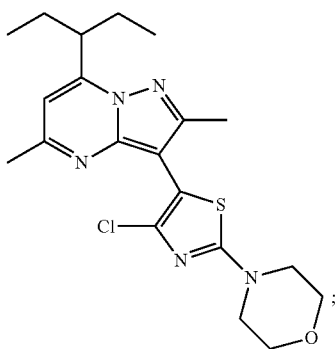 [SMILES: CCC(CC)c1cc(C)nc2c(-c3sc(N4CCOCC4)nc3Cl)c(C)nn12]

or a pharmaceutically acceptable salt or solvate thereof, wherein Compound 1 is administered at a dose between about 50 mg/day and about 1600 mg/day. In some embodiments, the metabolic symptoms are selected from the group consisting of body weight, BMI, waist circumference, blood pressure and glycemic control.

In one aspect, the present disclosure provides a method of improving quality of life in a subject in need thereof, comprising administering a pharmaceutical composition comprising Compound 1:

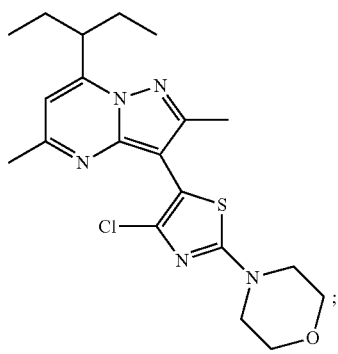 [SMILES: CCC(CC)c1cc(C)nc2c(-c3sc(N4CCOCC4)nc3Cl)c(C)nn12]

or a pharmaceutically acceptable salt or solvate thereof, wherein Compound 1 is administered at a dose between about 50 mg/day and about 1600 mg/day, wherein treatment results in an improved quality of life.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
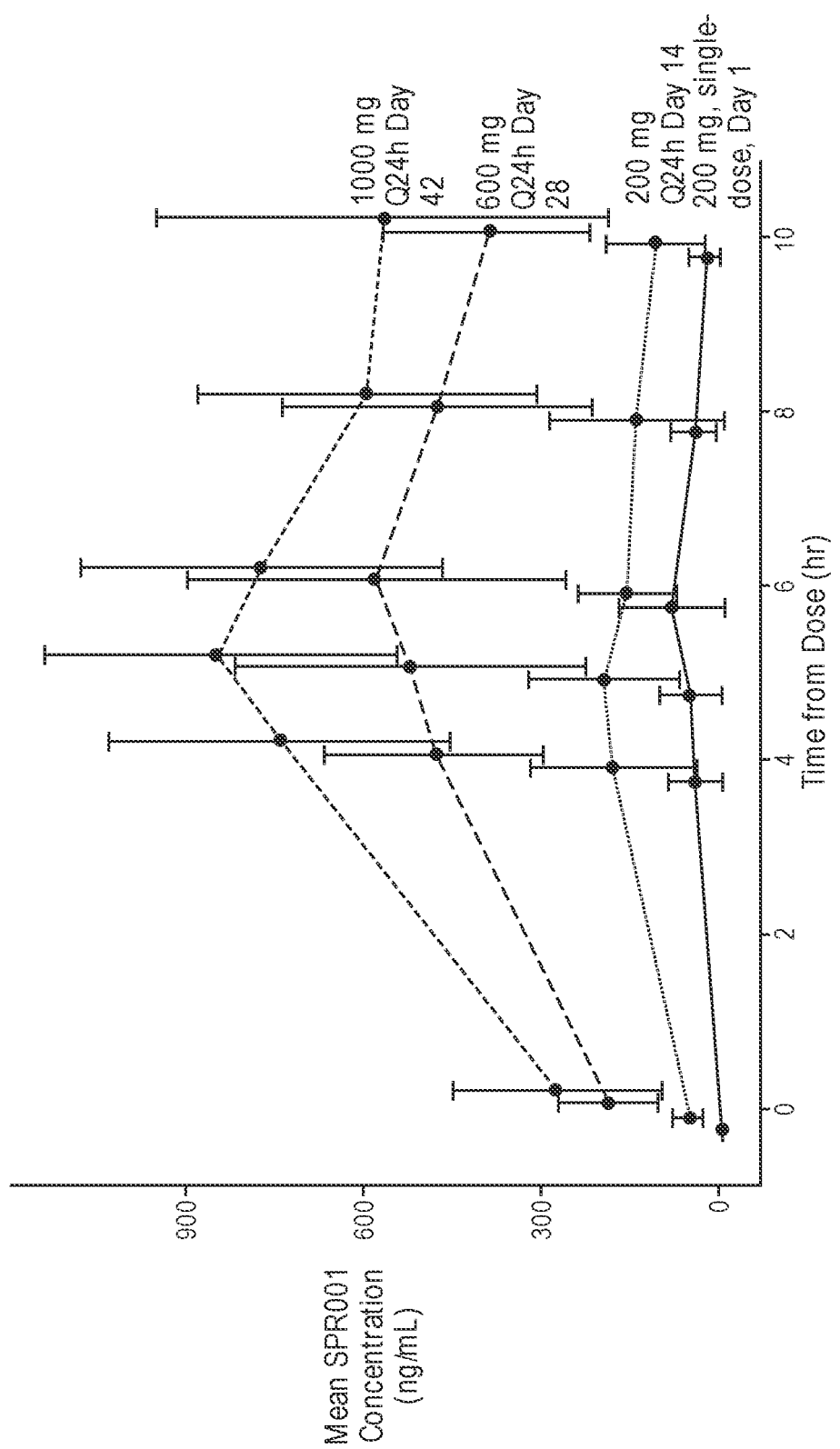
FIG. 1 shows Compound 1 in patients with CAH following 14-days of once daily dosing at each level.

CRF has been implicated in psychiatric disorders and neurological diseases including depression and anxiety, as well as the following: Alzheimer's disease, Huntington's disease, progressive supranuclear palsy, amyotrophic lateral sclerosis, Parkinson's disease, epilepsy, migraine, alcohol and substance abuse and associated withdrawal symptoms, obesity, metabolic syndrome, congenital adrenal hyperplasia (CAH), Cushing's disease, hypertension, stroke, irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary derived tumors, chronic fatigue syndrome, and fibromyalgia.

CRY receptor subtypes, CRF1 and CRF2, have been identified and are distributed heterogeneously within the brain thereby suggesting potential functional diversity. For example, widely distributed brain CRF1 receptors are strongly implicated in emotionality accompanying exposure to environmental stressors. Significantly, CRF1, not CRF2, receptors appear to mediate select anxiogenic like behaviors. A more discrete septallhypothalmic distribution and the availability of alternative endogenous ligands suggest a different functional role for the CRF2 receptor. For example, a novel CRF-family neuropeptide with preferential affinity for CRF2 relative to CRF1 receptors is reported to suppress appetite without producing the profile of behavioral activation observed with selective CRF1 agonism. In other cases, CRF2 agonism produces similar effects to those reported for CRF1 antagonists or CRF 1 gene deletion. For example, while CRF2 agonists have been proposed as antiobesity agents, CRF1 antagonists may be an important treatment for obesity as well.

Treatment of CAH is based on normalization of hormone and steroid levels using a variety of medications from diagnosis in infancy through adulthood. Glucocorticoids are the current standard treatment in CAH and are used both to correct the endogenous Cortisol deficiency and for reducing the elevated ACTH levels from the pituitary, which drives increased androgen production. Unlike the treatment of Addison's disease (adrenal insufficiency), in which Cortisol replacement is sufficient, the treatment of CAH must also reduce ACTH production, to control the subsequent androgen excess as well. Thus, the goals of glucocorticoid treatment include Cortisol replacement and suppression of ACTH to prevent virilization and menstrual disturbances in women. Mineralocorticoid replacement is needed to achieve normal plasma renin activity for maintenance of regular blood pressure, electrolyte balance, and volume status in those patients with the salt-wasting form of CAH.

The regimen of glucocorticoid treatment must support normal physiology and also ensure that sufficient Cortisol is available during events that may elicit a strong stress response (e.g., intercurrent illness, exercise, hypotension). Careful monitoring is also necessary to avoid the development of Addisonian syndrome due to under-treatment. Over-treatment with mineralocorticoids may cause hypertension while under-treatment may lead to low blood pressure, salt loss, fatigue and increased requirements for glucocorticoids. Typical laboratory tests for monitoring treatment efficacy include measurement of plasma concentrations of 17-OHP, androstenedione, testosterone, renin activity, and electrolytes.

Adult patients with CAH have an increased prevalence of risk factors for cardiovascular disease including obesity, hypertension, and insulin resistance. A study of a large cohort of pediatric and adult CAH patients (n=244) demonstrated that patients are prescribed a variety of glucocorticoid treatment regimens yet frequently suffer from poor hormonal control and the aforementioned adverse outcomes. Treatment of CAH includes efforts to normalize the Cortisol deficiency with glucocorticoids (usually hydrocortisone in children but often more potent agents with narrow therapeutic indices, such as dexamethasone, in adults) and, if necessary for salt-wasting, mineralocorticoids (usually fludrocortisone). The glucocorticoid doses required to achieve sufficient suppression of excess androgens, however, are usually well above the normal physiologic dose used for Cortisol replacement alone as in patients with Addison's disease. This increased exposure to glucocorticoids can lead to increased cardiovascular risk factors, glucose intolerance, and decreased bone mineral density in CAH patients.

CRF is believed to be the major physiological regulator of the basal and stress-induced release of adrenocorticotropic hormone ("ACTH"), β-endorphin, and other proopiomelanocortin ("POMC")-derived peptides from the anterior pituitary. Secretion of CRY causes release of ACTH from corticotrophs in the anterior pituitary via binding to the $CRF_1$ receptor, a member of the class B family of G-protein coupled receptors.

Due to the physiological significance of $CRF_1$, the development of biologically-active small molecules having significant CRY receptor binding activity and which are capable of antagonizing the $CRF_1$ receptor remains a desirable goal and has been the subject of ongoing research and development for the treatment of anxiety, depression, irritable bowel syndrome, post-traumatic stress disorder, and substance abuse.

The pituitary hormone ACTH, under the control of hypothalamic corticotropin-releasing factor (CRF), stimulates uptake of cholesterol and drives the synthesis of pregnenolone initiating steroidogenesis in the adrenal gland. The adrenal cortex is comprised of three zones, which produce distinct classes of hormones many of which are driven by ACTH mobilizing cholesterol through this pathway. Deficiencies in these enzymes as a result of mutation or deletion cause the substrate concentrations to increase. In the most common form of CAH resulting from mutations or deletions in the 21-hydroxylase gene (CYP21A2), potent androgens are produced by the adrenal because of the accumulation of the steroid precursors, progesterone and 17-hydroxyprogesterone (17-OHP). Plasma levels of 17-OHP can reach 10-1000 times the normal concentration in these cases. These increases result in the overproduction of androgens, specifically androstenedione, testosterone, and dihydroxytestosterone causing virilization in females. In addition, 21-hydroxylase deficiency in CAH causes insufficient biosynthesis of glucocorticoids and mineralocorticoids, specifically Cortisol and aldosterone. Cortisol is a critical negative feedback regulator of hypothalamic CRF secretion and pituitary ACTH release. The lack of glucocorticoid synthesis and release eliminates the restraint on the hypothalamus and pituitary, which causes ACTH levels to increase. The excessive ACTH stimulation causes hypertrophy of the zona fasciculata and zona reticularis resulting in adrenal hyperplasia.

In one embodiment, the CRF receptor antagonist useful for the treatment of CAH is 3-(4-Chloro-2-(morpholin-4-yl) thiazol-5-yl)-7-(1-ethylpropyl)-2,5-dimethylpyrazolo(1,5-a) pyrimidine.

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a," "an," and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. "Administering" a pharmaceutical composition may be accomplished by injection, topical administration, and oral administration or by other methods alone or in combination with other known techniques.

By "pharmaceutically acceptable", it is meant the carrier, diluent or excipient must be compatible with the other ingredients of the composition and not deleterious to the recipient thereof.

The term "pharmaceutical composition" means a composition comprising at least one active ingredient, such as Compound 1, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "supraphysiologic" amount" describes hormones levels that are elevated compared to average levels found in healthy individuals.

The term "physiologic amount" describes average hormone levels found in healthy individuals.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Compound

Disclosed herein is 3-(4-Chloro-2-(morpholin-4-yl)thiazol-5-yl)-7-(1-ethylpropyl)-2,5-dimethylpyrazolo(1,5-a)pyrimidine (or alternatively 4-(4-chloro-5-(2,5-dimethyl-7-(pentan-3-yl)pyrazolo[1,5-a]pyrimidin-3-yl)thiazol-2-yl)morpholine), a pharmaceutically acceptable salt, and/or a solvate thereof:

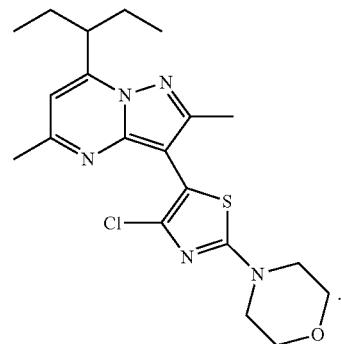

In some embodiments, 4-(4-chloro-5-(2,5-dimethyl-7-(pentan-3-yl)pyrazolo[1,5-a]pyrimidin-3-yl)thiazol-2-yl)morpholine is referred to as Compound 1. In some embodiments, 3-(4-Chloro-2-(morpholin-4-yl)thiazol-5-yl)-7-(1-ethylpropyl)-2,5-dimethylpyrazolo(1,5-a)pyrimidine is referred to as Compound 1.

Pharmaceutical Compositions

Disclosed herein is a pharmaceutical composition comprising Compound 1, a pharmaceutically acceptable salt, and/or a solvate thereof.

Dosage Form

In some embodiments, the pharmaceutical compositions described herein are provided in unit dosage form. As used herein, a "unit dosage form" is a composition containing an amount of Compound 1 that is suitable for administration to an animal, preferably mammal, subject in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical compositions described herein are formulated as oral dosage forms. Suitable oral dosage forms include, for example, tablets, pills, sachets, or capsules. In some embodiments, the pharmaceutical composition comprises one or more additional pharmaceutically acceptable excipients. See, e.g., *Remington: The Science and Practice of Pharmacy* (Gennaro, 21$^{st}$ Ed. Mack Pub. Co., Easton, PA (2005) for a list of pharmaceutically acceptable excipients.

Capsule

In some embodiments, the pharmaceutical composition is formulated as a capsule. In some embodiments, the pharmaceutical composition is formulated as a hard gel capsule. In some embodiments, the pharmaceutical composition is formulated as a soft gel capsule.

In some embodiments, the capsule is formed using materials which include, but are not limited to, natural or synthetic gelatin, pectin, casein, collagen, protein, modified starch, polyvinylpyrrolidone, acrylic polymers, cellulose derivatives, or any combinations thereof. In some embodiments, the capsule is formed using preservatives, coloring and opacifying agents, flavorings and sweeteners, sugars, gastroresistant substances, or any combinations thereof. In some embodiments, the capsule is coated. In some embodiments, the coating covering the capsule includes, but is not limited to, immediate release coatings, protective coatings, enteric or delayed release coatings, sustained release coatings, barrier coatings, seal coatings, or combinations thereof. In some embodiments, a capsule herein is hard or soft. In some embodiments, the capsule is seamless. In some embodiments, the capsule is broken such that the particulates are sprinkled on soft foods and swallowed without chewing. In some embodiments, the shape and size of the capsule also vary. Examples of capsule shapes include, but are not limited to, round, oval, tubular, oblong, twist off, or a non-standard shape. The size of the capsule may vary according to the volume of the particulates. In some embodiments, the size of the capsule is adjusted based on the volume of the particulates and powders. Hard or soft gelatin capsules may be manufactured in accordance with conventional methods as a single body unit comprising the standard capsule shape. A single-body soft gelatin capsule typically may be provided, for example, in sizes from 3 to 22 minims (1 minims being equal to 0.0616 ml) and in shapes of oval, oblong or others. The gelatin capsule may also be manufactured in accordance with conventional methods, for example, as a two-piece hard gelatin capsule, sealed or unsealed, typically in standard shape and various standard sizes, conventionally designated as (000), (00), (0), (1), (2), (3), (4), and (5). The largest number corresponds to the smallest size. In some embodiments, the pharmaceutical composition described herein (e.g., capsule) is swallowed as a whole.

In some embodiments, the capsule comprises one or more pharmaceutically acceptable excipients. In some embodiments, the capsule is free of additional excipients.

In some embodiments, a capsule is developed, manufactured and commercialized for a drug substance that is insoluble. In some embodiments, a drug substance is insoluble if solubility is less than 0.002 mg/mL in water. In some embodiments, the capsule has a dose strength of up to 200 mg. In some embodiments, drug substance in the capsule is immediately released in a dissolution medium using USP apparatus I. In some embodiments, drug substance in the capsule is immediately released in a dissolution medium using USP apparatus II.

Tablet

Poorly soluble drugs may be difficult to formulate using standard technologies such as high shear wet granulation. Optimum delivery of poorly soluble drugs may require complex technologies such as solid solutions amorphous dispersions (hot melt extrusion or spray drying), nano-formulations or lipid-based formulations. Hydrophobic drug substances may be considered poorly soluble according to USP criteria and may be known to be difficult to granulate with water and other excipients. This is likely due to most known excipients for immediate release formulations being water soluble or water-swellable. Making a tablet of a high dose drug substance that is poorly soluble may require a high concentration of the drug substance. However, as the drug concentration is increased above a certain level, formation of granules may become more and more difficult. Furthermore, at a certain drug load, it may become impossible.

In some embodiments, the pharmaceutical composition is formulated as a tablet.

In some embodiments, the tablet is made by compression, molding, or extrusion, optionally with one or more pharmaceutically acceptable excipient. In some embodiments, compressed tablets are prepared by compressing Compound 1 in a free-flowing form, optionally mixed with pharmaceutically acceptable excipients. In some embodiments, molded tablets are made by molding a mixture of the powdered Compound 1 moistened with an inert liquid diluent. In some embodiments, the tablet is prepared by hot-melt extrusion. In some embodiments, extruded tablets are made by forcing a mixture comprising Compound 1 through an orifice or die under controlled conditions. In some embodiments, the tablet is coated or scored. In some embodiments, the tablet is formulated so as to provide slow or controlled release of Compound 1. In some embodiments, a tablet is developed, manufactured and commercialized for a drug substance that is insoluble. In some embodiments, a drug substance is insoluble if solubility is less than 0.002 mg/mL in water. In some embodiments, the tablet has a dose strength of up to 200 mg. In some embodiments, drug substance in the tablet is immediately released in a dissolution medium using USP apparatus I. In some embodiments, drug substance in the tablet is immediately released in a dissolution medium using USP apparatus II.

In some embodiments, the tablet size is less than about 1000 mg, less than about 800 mg, less than about 600 mg, less than about 400 mg or less than about 200 mg. In some embodiments, the tablet has a dose strength of more than about 50 mg, more than about 100 mg, more than about 150 mg, more than about 200 mg, or more than about 250 mg. In some embodiments, the tablet size is less than about 1000 mg for a dose strength of more than about 50 mg. In some embodiments, the tablet size is less than 800 mg for a dose strength of more than about 100 mg. In some embodiments, the tablet size is less than 600 mg for a dose strength of more than about 150 mg. In some embodiment, the tablet size is less than 400 mg for a dose strength of more than about 200 mg. In some embodiments, the tablet size is less than 400 mg for a dose strength of 200 mg.

In some embodiments, more than about 20% of the tablet is dissolved in conventional dissolution media. In some embodiments, more than about 40% of the tablet is dissolved in conventional dissolution media. In some embodiments, more than about 50% of the tablet is dissolved in conventional dissolution media. In some embodiments, more than about 60% of the tablet is dissolved in conventional dissolution media. In some embodiments, more than about 70% of the tablet is dissolved in conventional dissolution media. In some embodiments, more than about 80% of the tablet is dissolved in conventional dissolution media. In some embodiments, more than about 20% of the tablet is dissolved in less than 24 hours in conventional dissolution media. In some embodiments, more than about 20% of the tablet is dissolved in less than 12 hours in conventional dissolution media. In some embodiments, more than about 20% of the tablet is dissolved in less than 6 hours in conventional dissolution media. In some embodiments, more than about 20% of the tablet is dissolved in less than 3 hours in conventional dissolution media. In some embodiments, more than about 20% of the tablet is dissolved in less than 2 hours in conventional dissolution media. In some embodiments, more than about 20% of the tablet is dissolved in less than 60 minutes in conventional dissolution media. In some embodiments, more than about 40% of the tablet is dissolved in less than 60 minutes in conventional dissolution media. In some embodiments, more than about 50% of the tablet is dissolved in less than 60 minutes in conventional dissolution media. In some embodiments, more than about 60% of the tablet is dissolved in less than 60 minutes in conventional dissolution media. In some embodiments, more than about 70% of the tablet is dissolved in less than 60 minutes in conventional dissolution media. In some embodiments, more than about 80% of the tablet is dissolved in less than 60 minutes in conventional dissolution media. In some embodiments, more than 70% of the tablet is dissolved in 60 minutes in conventional dissolution media.

In some embodiments, the tablet is produced at a commercial scale.

In some embodiments, the tablet comprises one or more pharmaceutically acceptable excipients.

In some embodiments, the tablet is coated with a coating material, e.g., a sealant. In some embodiments, the coating material is water soluble. In some embodiments, the coating material comprises a polymer, plasticizer, a pigment, or any combination thereof. In some embodiments, the coating material is in the form of a film coating, e.g., a glossy film, a pH independent film coating, an aqueous film coating, a dry powder film coating (e.g., complete dry powder film coating), or any combination thereof. In some embodiments, the coating material is highly adhesive. In some embodiments, the coating material provides low level of water permeation. In some embodiments, the coating material provides oxygen barrier protection. In some embodiments, the coating material allows immediate disintegration for fast release of Compound 1. In some embodiments, the coating material is pigmented, clear, or white. In some embodiments, the coating is an enteric coating. Exemplary coating materials include, without limitation, polyvinylpyrrolidone, polyvinyl alcohol, an acrylate-methacrylic acid copolymer, a methacrylate-methacrylic acid copolymer, cellulose acetate phthalate, cellulose acetate succinate, hydroxypropyl methylcellulose phthalate, hydroxypropyl methylcellulose acetate succinate, polyvinyl acetate phthalate, shellac, cellulose acetate trimellitate, sodium alginate, zein, and any combinations thereof.

Pharmaceutically Acceptable Excipients

In some embodiments, the pharmaceutical composition comprises a pharmaceutically acceptable excipient. In some embodiments, the composition is free of pharmaceutically acceptable excipients. The term "pharmaceutically acceptable excipient", as used herein, means one or more compatible solid or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. In some embodiments, the pharmaceutically acceptable excipient is of sufficiently high purity and sufficiently low toxicity to render them suitable for administration preferably to an animal, preferably mammal, being treated.

Some examples of substances, which can serve as pharmaceutically acceptable excipients include:

Amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments, the amino acid is arginine. In some embodiments, the amino acid is L-arginine.

Monosaccharides such as glucose (dextrose), arabinose, mannitol, fructose (levulose), and galactose.

Cellulose and its derivatives such as sodium carboxymethyl cellulose, ethyl cellulose, and methyl cellulose.

Solid lubricants such as talc, stearic acid, magnesium stearate, and sodium stearyl fumarate.

Polyols such as propylene glycol, glycerin, sorbitol, mannitol, and polyethylene glycol.

Emulsifiers such as the polysorbates.

Wetting agents such as sodium lauryl sulfate, Tween®, Span, alkyl sulphates, and alkyl ethoxylate sulphates.

Diluents such as calcium carbonate, microcrystalline cellulose, calcium phosphate, starch, pregelatinized starch, sodium carbonate, mannitol, and lactose.

Binders such as starches (corn starch and potato starch), gelatin, sucrose, hydroxypropyl cellulose (HPC), polyvinylpyrrolidone (PVP), and hydroxypropyl methyl cellulose (HPMC).

Disintegrants such as starch, and alginic acid.

Super-disintegrants such as ac-di-sol, croscarmellose sodium, sodium starch glycolate and crospovidone.

Glidants such as silicon dioxide.

Coloring agents such as the FD&C dyes.

Sweeteners and flavoring agents, such as aspartame, saccharin, menthol, peppermint, and fruit flavors.

Preservatives such as benzalkonium chloride, PHMB, chlorobutanol, thimerosal, phenylmercuric, acetate, phenylmercuric nitrate, parabens, and sodium benzoate.

Tonicity adjustors such as sodium chloride, potassium chloride, mannitol, and glycerin.

Antioxidants such as sodium bisulfite, acetone sodium bisulfite, sodium formaldehyde, sulfoxylate, thiourea, and EDTA.

pH adjuster such as NaOH, sodium carbonate, sodium acetate, HCl, and citric acid.

Cryoprotectants such as sodium or potassium phosphates, citric acid, tartaric acid, gelatin, and carbohydrates such as dextrose, mannitol, and dextran.

Cationic surfactants such as cetrimide, benzalkonium chloride and cetylpyridinium chloride.

Anion surfactants such as alkyl sulphates, alkyl ethoxylate sulphates, soaps, carboxylates, sulfates, and sulfonates.

Non-ionic surfactants such as polyoxyethylene derivatives, polyoxypropylene derivatives, polyol derivatives, polyol esters, polyoxyethylene esters, poloxamers, glyol esters, glycerol esters, sorbitan derivatives, polyethylene glycol (PEG-40, PEG-50, PEG-55), and ethers of fatty alcohols.

Organic materials such as carbohydrate and modified carbohydrates, lactose, a-lactose monohydrate, spray dried lactose and anhydrous lactose, starch and pre-gelatinized starch, sucrose, manitol, sorbitol, cellulose, powdered cellulose and microcrystalline cellulose.

Inorganic materials such as calcium phosphates (anhydrous dibasic calcium phosphate, dibasic calcium phosphate and tribasic calcium phosphate).

Co-processed diluents.

Surfactants such as sodium lauryl sulfate.

Compression aids.

Anti-tacking agents such as silicon dioxide and talc

Amounts

In some embodiments, the pharmaceutical composition, in the form of a tablet or capsule, comprises between about 1 mg and about 500 mg of Compound 1, or a pharmaceutically acceptable salt or solvate thereof. In some embodiments, the pharmaceutical composition, in the form of a tablet or capsule, comprises between about 1 mg and about 500 mg of Compound 1, or a pharmaceutically acceptable salt or solvate thereof. In some embodiments, the pharmaceutical composition, in the form of a tablet or capsule, comprises between about 1 mg and about 400 mg of Compound 1, or a pharmaceutically acceptable salt or solvate thereof. In some embodiments, the pharmaceutical composition, in the form of a tablet or capsule, comprises between about 1 mg and about 300 mg of Compound 1, or a pharmaceutically acceptable salt or solvate thereof. In some embodiments, the pharmaceutical composition, in the form of a tablet or capsule, comprises between about 1 mg and about 200 mg of Compound 1, or a pharmaceutically acceptable salt or solvate thereof. In some embodiments, the pharmaceutical composition, in the form of a tablet or capsule, comprises between about 1 mg and about 100 mg of Compound 1, or a pharmaceutically acceptable salt or solvate thereof. In some embodiments, the pharmaceutical composition, in the form of a tablet or capsule, comprises between about 1 mg and about 90 mg of Compound 1, or a pharmaceutically acceptable salt or solvate thereof. In some embodiments, the pharmaceutical composition, in the form of a tablet or capsule, comprises between about 1 mg and about 80 mg of Compound 1, or a pharmaceutically acceptable salt or solvate thereof. In some embodiments, the pharmaceutical composition, in the form of a tablet or capsule, comprises between about 1 mg and about 70 mg of Compound 1, or a pharmaceutically acceptable salt or solvate thereof. In some embodiments, the pharmaceutical composition, in the form of a tablet or capsule, comprises between about 1 mg and about 60 mg of Compound 1, or a pharmaceutically acceptable salt or solvate thereof. In some embodiments, the pharmaceutical composition, in the form of a tablet or capsule, comprises between about 1 mg and about 50 mg of Compound 1, or a pharmaceutically acceptable salt or solvate thereof. In some embodiments, the pharmaceutical composition, in the form of a tablet or capsule, comprises between about 1 mg and about 40 mg of Compound 1, or a pharmaceutically acceptable salt or solvate thereof. In some embodiments, the pharmaceutical composition, in the form of a tablet or capsule, comprises between about 1 mg and about 30 mg of Compound 1, or a pharmaceutically acceptable salt or solvate thereof. In some embodiments, the pharmaceutical composition, in the form of a tablet or capsule, comprises between about 1 mg and about 20 mg of Compound 1, or a pharmaceutically acceptable salt or solvate thereof. In some embodiments, the pharmaceutical composition, in the form of a tablet or capsule, comprises between about 1 mg and about 10 mg of Compound 1, or a pharmaceutically acceptable salt or solvate thereof. In some embodiments, the pharmaceutical composition, in the form of a tablet or capsule, comprises between about 1 mg and about 5 mg of Compound 1, or a pharmaceutically acceptable salt or solvate thereof. In some embodiments, the pharmaceutical composition, in the form of a tablet or capsule comprises about 1 mg of Compound 1, or a pharmaceutically acceptable salt or solvate thereof. In some embodiments, the pharmaceutical composition, in the form of a tablet or capsule comprises about 5 mg of Compound 1, or a pharmaceutically acceptable salt or solvate thereof.

In some embodiments, the pharmaceutical composition, in the form of a tablet or capsule, comprises between about 1 mg and about 500 mg of Compound 1, or a pharmaceutically acceptable salt or solvate thereof. In some embodiments, the pharmaceutical composition, in the form of a tablet or capsule, comprises between about 5 mg and about 500 mg of Compound 1, or a pharmaceutically acceptable salt or solvate thereof. In some embodiments, the pharmaceutical composition, in the form of a tablet or capsule, comprises between about 10 mg and about 500 mg of Compound 1, or a pharmaceutically acceptable salt or solvate thereof. In some embodiments, the pharmaceutical composition, in the form of a tablet or capsule, comprises between about 10 mg and about 400 mg of Compound 1, or a pharmaceutically acceptable salt or solvate thereof. In some embodiments, the pharmaceutical composition, in the form of a tablet or capsule, comprises between about 10 mg and about 300 mg of Compound 1, or a pharmaceutically acceptable salt or solvate thereof. In some embodiments, the pharmaceutical composition, in the form of a tablet or capsule, comprises between about 10 mg and about 200 mg of Compound 1, or a pharmaceutically acceptable salt or solvate thereof. In some embodiments, the pharmaceutical composition, in the form of a tablet or capsule, comprises between about 10 mg and about 100 mg of Compound 1, or a pharmaceutically acceptable salt or solvate thereof. In some embodiments, the pharmaceutical composition, in the form of a tablet or capsule, comprises between about 10 mg and about 90 mg of Compound 1, or a pharmaceutically acceptable salt or solvate thereof. In some embodiments, the pharmaceutical composition, in the form of a tablet or capsule, comprises between about 10 mg and about 80 mg of Compound 1, or a pharmaceutically acceptable salt or solvate thereof. In some embodiments, the pharmaceutical composition, in the form of a tablet or capsule, comprises between about 10 mg and about 70 mg of Compound 1, or a pharmaceutically acceptable salt or solvate thereof. In some embodiments, the pharmaceutical composition, in the form of a tablet or capsule, comprises between about 10 mg and about 60 mg of Compound 1, or a pharmaceutically acceptable salt or solvate thereof.

In some embodiments, the pharmaceutical composition, in the form of a tablet or capsule, comprises between about 20 mg and about 500 mg of Compound 1, or a pharmaceutically acceptable salt or solvate thereof. In some embodiments, the pharmaceutical composition, in the form of a tablet or capsule, comprises between about 20 mg and about 400 mg of Compound 1, or a pharmaceutically acceptable salt or solvate thereof. In some embodiments, the pharmaceutical composition, in the form of a tablet or capsule, comprises between about 20 mg and about 300 mg of Compound 1, or a pharmaceutically acceptable salt or solvate thereof. In some embodiments, the pharmaceutical composition, in the form of a tablet or capsule, comprises between about 20 mg and about 200 mg of Compound 1, or a pharmaceutically acceptable salt or solvate thereof. In some embodiments, the pharmaceutical composition, in the form of a tablet or capsule, comprises between about 20 mg and about 100 mg of Compound 1, or a pharmaceutically acceptable salt or solvate thereof. In some embodiments, the pharmaceutical composition, in the form of a tablet or capsule, comprises between about 20 mg and about 90 mg of Compound 1, or a pharmaceutically acceptable salt or solvate thereof. In some embodiments, the pharmaceutical composition, in the form of a tablet or capsule, comprises between about 20 mg and about 80 mg of Compound 1, or a pharmaceutically acceptable salt or solvate thereof. In some embodiments, the pharmaceutical composition, in the form of a tablet or capsule, comprises between about 20 mg and about 70 mg of Compound 1, or a pharmaceutically acceptable salt or solvate thereof. In some embodiments, the pharmaceutical composition, in the form of a tablet or capsule, comprises between about 20 mg and about 60 mg of Compound 1, or a pharmaceutically acceptable salt or solvate thereof.

In some embodiments, the pharmaceutical composition, in the form of a tablet or capsule, comprises between about 30 mg and about 500 mg of Compound 1, or a pharmaceutically acceptable salt or solvate thereof. In some embodiments, the pharmaceutical composition, in the form of a tablet or capsule, comprises between about 30 mg and about 400 mg of Compound 1, or a pharmaceutically acceptable salt or solvate thereof. In some embodiments, the pharmaceutical composition, in the form of a tablet or capsule, comprises between about 30 mg and about 300 mg of Compound 1, or a pharmaceutically acceptable salt or solvate thereof. In some embodiments, the pharmaceutical composition, in the form of a tablet or capsule, comprises between about 30 mg and about 200 mg of Compound 1, or a pharmaceutically acceptable salt or solvate thereof. In some embodiments, the pharmaceutical composition, in the form of a tablet or capsule, comprises between about 30 mg and about 100 mg of Compound 1, or a pharmaceutically acceptable salt or solvate thereof. In some embodiments, the pharmaceutical composition, in the form of a tablet or capsule, comprises between about 30 mg and about 90 mg of Compound 1, or a pharmaceutically acceptable salt or solvate thereof. In some embodiments, the pharmaceutical composition, in the form of a tablet or capsule, comprises between about 30 mg and about 80 mg of Compound 1, or a pharmaceutically acceptable salt or solvate thereof. In some embodiments, the pharmaceutical composition, in the form of a tablet or capsule, comprises between about 30 mg and about 70 mg of Compound 1, or a pharmaceutically acceptable salt or solvate thereof. In some embodiments, the pharmaceutical composition, in the form of a tablet or capsule, comprises between about 30 mg and about 60 mg of Compound 1, or a pharmaceutically acceptable salt or solvate thereof.

In some embodiments, the pharmaceutical composition, in the form of a tablet or capsule, comprises between about 40 mg and about 500 mg of Compound 1, or a pharmaceutically acceptable salt or solvate thereof. In some embodiments, the pharmaceutical composition, in the form of a tablet or capsule, comprises between about 40 mg and about 400 mg of Compound 1, or a pharmaceutically acceptable salt or solvate thereof. In some embodiments, the pharmaceutical composition, in the form of a tablet or capsule, comprises between about 40 mg and about 300 mg of Compound 1, or a pharmaceutically acceptable salt or solvate thereof. In some embodiments, the pharmaceutical composition, in the form of a tablet or capsule, comprises between about 40 mg and about 200 mg of Compound 1, or a pharmaceutically acceptable salt or solvate thereof. In some embodiments, the pharmaceutical composition, in the form of a tablet or capsule, comprises between about 40 mg and about 100 mg of Compound 1, or a pharmaceutically acceptable salt or solvate thereof. In some embodiments, the pharmaceutical composition, in the form of a tablet or capsule, comprises between about 40 mg and about 90 mg of Compound 1, or a pharmaceutically acceptable salt or solvate thereof. In some embodiments, the pharmaceutical composition, in the form of a tablet or capsule, comprises between about 40 mg and about 80 mg of Compound 1, or a pharmaceutically acceptable salt or solvate thereof. In some embodiments, the pharmaceutical composition, in the form of a tablet or capsule, comprises between about 40 mg and about 70 mg of Compound 1, or a pharmaceutically acceptable salt or solvate thereof. In some embodiments, the pharmaceutical composition, in the form of a tablet or capsule, comprises between about 40 mg and about 60 mg of Compound 1, or a pharmaceutically acceptable salt or solvate thereof. In some embodiments, the pharmaceutical composition, in the form of a tablet or capsule, comprises about 50 mg of Compound 1, or a pharmaceutically acceptable salt or solvate thereof.

In some embodiments, the pharmaceutical composition, in the form of a tablet or capsule, comprises between about 50 mg and about 500 mg of Compound 1, or a pharmaceutically acceptable salt or solvate thereof. In some embodiments, the pharmaceutical composition, in the form of a tablet or capsule, comprises between about 50 mg and about 400 mg of Compound 1, or a pharmaceutically acceptable salt or solvate thereof. In some embodiments, the pharmaceutical composition, in the form of a tablet or capsule, comprises between about 50 mg and about 300 mg of Compound 1, or a pharmaceutically acceptable salt or solvate thereof. In some embodiments, the pharmaceutical composition, in the form of a tablet or capsule, comprises between about 50 mg and about 200 mg of Compound 1, or a pharmaceutically acceptable salt or solvate thereof. In some embodiments, the pharmaceutical composition, in the form of a tablet or capsule, comprises between about 50 mg and about 100 mg of Compound 1, or a pharmaceutically acceptable salt or solvate thereof. In some embodiments, the pharmaceutical composition, in the form of a tablet or capsule, comprises between about 50 mg and about 90 mg of Compound 1, or a pharmaceutically acceptable salt or solvate thereof. In some embodiments, the pharmaceutical composition, in the form of a tablet or capsule, comprises between about 50 mg and about 80 mg of Compound 1, or a pharmaceutically acceptable salt or solvate thereof. In some embodiments, the pharmaceutical composition, in the form of a tablet or capsule, comprises between about 50 mg and about 70 mg of Compound 1, or a pharmaceutically acceptable salt or solvate thereof.

In some embodiments, the pharmaceutical composition comprises between about 100 mg and about 500 mg of Compound 1, or a pharmaceutically acceptable salt or solvate thereof. In some embodiments, the pharmaceutical composition comprises between about 100 mg and about 400 mg of Compound 1, or a pharmaceutically acceptable salt or solvate thereof. In some embodiments, the pharmaceutical composition comprises between about 100 mg and about 300 mg of Compound 1, or a pharmaceutically acceptable salt or solvate thereof. In some embodiments, the pharmaceutical composition comprises between about 150 mg and about 250 mg of Compound 1, or a pharmaceutically acceptable salt or solvate thereof. In some embodiments, the pharmaceutical composition comprises between about 100 mg and about 200 mg of Compound 1, or a pharmaceutically acceptable salt or solvate thereof.

In some embodiments, the pharmaceutical composition comprises about 500 mg of Compound 1, or a pharmaceutically acceptable salt or solvate thereof. In some embodiments, the pharmaceutical composition comprises about 400 mg of Compound 1, or a pharmaceutically acceptable salt or solvate thereof. In some embodiments, the pharmaceutical composition comprises about 300 mg of Compound 1, or a pharmaceutically acceptable salt or solvate thereof. In some embodiments, the pharmaceutical composition comprises about 250 mg of Compound 1, or a pharmaceutically acceptable salt or solvate thereof. In some embodiments, the pharmaceutical composition comprises about 200 mg of Compound 1, or a pharmaceutically acceptable salt or solvate thereof. In some embodiments, the pharmaceutical composition comprises about 150 mg of Compound 1, or a pharmaceutically acceptable salt or solvate thereof. In some embodiments, the pharmaceutical composition comprises about 100 mg of Compound 1, or a pharmaceutically acceptable salt or solvate thereof. In some embodiments, the pharmaceutical composition comprises about 90 mg of Compound 1, or a pharmaceutically acceptable salt or solvate thereof. In some embodiments, the pharmaceutical composition comprises about 80 mg of Compound 1, or a pharmaceutically acceptable salt or solvate thereof. In some embodiments, the pharmaceutical composition comprises about 70 mg of Compound 1, or a pharmaceutically acceptable salt or solvate thereof. In some embodiments, the pharmaceutical composition comprises about 60 mg of Compound 1, or a pharmaceutically acceptable salt or solvate thereof. In some embodiments, the pharmaceutical composition comprises about 50 mg of Compound 1, or a pharmaceutically acceptable salt or solvate thereof. In some embodiments, the pharmaceutical composition comprises about 40 mg of Compound 1, or a pharmaceutically acceptable salt or solvate thereof. In some embodiments, the pharmaceutical composition comprises about 30 mg of Compound 1, or a pharmaceutically acceptable salt or solvate thereof. In some embodiments, the pharmaceutical composition comprises about 20 mg of Compound 1, or a pharmaceutically acceptable salt or solvate thereof. In some embodiments, the pharmaceutical composition comprises about 10 mg of Compound 1, or a pharmaceutically acceptable salt or solvate thereof.

Particle Size

In some embodiments, the pharmaceutical composition, in the form of a tablet or a capsule, comprises Compound 1, or a pharmaceutically acceptable salt or solvate thereof, in the form of microparticles. In some embodiments, microparticles of Compound 1 have an average size from about 1 µm to about 100 µm. In some embodiments, microparticles of Compound 1 have an average size from about 1 µm to about 50 µm. In some embodiments, microparticles of Compound 1 have an average size from about 1 µm to about 30 µm. In some embodiments, microparticles of Compound 1 have an average size from about 1 µm to about 20 µm. In some embodiments, microparticles of Compound 1 have an average size from about 5 µm to about 15 µm. In some embodiments, microparticles of Compound 1 have an average size from about 1 µm to about 10 µm. In some embodiments, microparticles of Compound 1 have an average size from about 3 µm to about 10 µm. In some embodiments, microparticles of Compound 1 have an average size from about 4 µm to about 9 µm.

In some embodiments, microparticles of Compound 1 have an average size less than about 100 µm. In some embodiments, microparticles of Compound 1 have an average size less than about 80 µm. In some embodiments, microparticles of Compound 1 have an average size less than about 60 µm. In some embodiments, microparticles of Compound 1 have an average size less than about 50 µm. In some embodiments, microparticles of Compound 1 have an average size less than about 40 µm. In some embodiments, microparticles of Compound 1 have an average size less than about 30 µm. In some embodiments, microparticles of Compound 1 have an average size less than about 20 µm. In some embodiments, microparticles of Compound 1 have an average size less than about 10 µm.

Pharmacokinetics

In some embodiments, Compound 1 is formulated as a capsule or a tablet as to provide a Tmax of about 1 to about 8 hours in a subject. In some embodiments, Compound 1 is formulated as a capsule or a tablet as to provide a Tmax of about 2 to about 7 hours in a subject. In some embodiments, Compound 1 is formulated as a capsule or a tablet as to provide a Tmax of about 2 to about 6 hours in a subject. In some embodiments, Compound 1 is formulated as a capsule or a tablet as to provide a Tmax of about 3 to about 5 hours in a subject.

In some embodiments, Compound 1 is formulated as a capsule or a tablet as to provide a Tmax of about 8 hours in a subject. In some embodiments, Compound 1 is formulated as a capsule or a tablet as to provide a Tmax of about 7 hours in a subject. In some embodiments, Compound 1 is formulated as a capsule or a tablet as to provide a Tmax of about 6 hours in a subject. In some embodiments, Compound 1 is formulated as a capsule or a tablet as to provide a Tmax of about 5 hours in a subject. In some embodiments, Compound 1 is formulated as a capsule or a tablet as to provide a Tmax of about 4 hours in a subject. In some embodiments, Compound 1 is formulated as a capsule or a tablet as to provide a Tmax of about 3 hours in a subject. In some embodiments, Compound 1 is formulated as a capsule or a tablet as to provide a Tmax of about 2 hours in a subject. In some embodiments, Compound 1 is formulated as a capsule or a tablet as to provide a Tmax of about 1 hour in a subject.

Stability

The pharmaceutical compositions described herein are stable in various storage conditions including refrigerated, ambient and accelerated conditions. Stable as used herein refers to pharmaceutical compositions having about 95% or greater of the initial Compound 1 amount and about 5% w/w or less total impurities or related substances at the end of a given storage period. The percentage of impurities is calculated from the amount of impurities relative to the amount of Compound 1. Stability is assessed by HPLC or any other known testing method. In some embodiments, the stable pharmaceutical compositions have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable pharmaceutical compositions have about 5% w/w total impurities or related substances. In yet other embodiments, the stable pharmaceutical compositions have about 4% w/w total impurities or related substances. In yet other embodiments, the stable pharmaceutical compositions have about 3% w/w total impurities or related substances. In yet other embodiments, the stable pharmaceutical compositions have about 2% w/w total impurities or related substances. In yet other embodiments, the stable pharmaceutical compositions have about 1% w/w total impurities or related substances.

At refrigerated condition, the pharmaceutical compositions described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, refrigerated condition is 5±5° C. In some embodiments, refrigerated condition is about 0° C., about 0.1° C., about 0.2° C., about 0.3° C., about 0.4° C., about 0.5° C., about 0.6° C., about 0.7° C., about 0.8° C., about 0.9° C., about 1° C., about 1.1° C., about 1.2° C., about 1.3° C., about 1.4° C., about 1.5° C., about 1.6° C., about 1.7° C., about 1.8° C., about 1.9° C., about 2° C., about 2.1° C., about 2.2° C., about 2.3° C., about 2.4° C., about 2.5° C., about 2.6° C., about 2.7° C., about 2.8° C., about 2.9° C., about 3° C., about 3.1° C., about 3.2° C., about 3.3° C., about 3.4° C., about 3.5° C., about 3.6° C., about 3.7° C., about 3.8° C., about 3.9° C., about 4° C., about 4.1° C., about 4.2° C., about 4.3° C., about 4.4° C., about 4.5° C., about 4.6° C., about 4.7° C., about 4.8° C., about 4.9° C., about 5° C., about 5.1° C., about 5.2° C., about 5.3° C., about 5.4° C., about 5.5° C., about 5.6° C., about 5.7° C., about 5.8° C., about 5.9° C., about 6° C., about 6.1° C., about 6.2° C., about 6.3° C., about 6.4° C., about 6.5° C., about 6.6° C., about 6.7° C., about 6.8° C., about 6.9° C., about 7° C., about 7.1° C., about 7.2° C., about 7.3° C., about 7.4° C., about 7.5° C., about 7.6° C., about 7.7° C., about 7.8° C., about 7.9° C., about 8° C., about 8.1° C., about 8.2° C., about 8.3° C., about 8.4° C., about 8.5° C., about 8.6° C., about 8.7° C., about 8.8° C., about 8.9° C., about 9° C., about 9.1° C., about 9.2° C., about 9.3° C., about 9.4° C., about 9.5° C., about 9.6° C., about 9.7° C., about 9.8° C., about 9.9° C., or about 10° C. At accelerated conditions, the pharmaceutical compositions described herein are stable for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 month. Accelerated conditions for the pharmaceutical compositions described herein include temperatures that are at or above ambient levels (e.g. 25±5° C.). In some instances, an accelerated condition is at about 40±2° C. In some instances, an accelerated condition is at about 35° C., about 40° C., about 45° C., about 50° C., about 55° C., or about 60° C. Accelerated conditions for the pharmaceutical compositions described herein also include relative humidity (RH) that are at or above ambient levels (55±10% RH). In other instances, an accelerated condition is above about 65% RH, about 70% RH, about 75% RH, or about 80% RH. In further instances, an accelerated condition is about 40° C. or 60° C. at ambient humidity. In yet further instances, an accelerated condition is about 40±2° C. at 75±5% RH humidity.

In some embodiments, the pharmaceutical compositions are stable at about 5±5° C. to about 25±5° C. for at least 12 months. In one embodiment, the pharmaceutical compositions are stable at about 5±5° C. for at least 12 months. In one embodiment, the pharmaceutical compositions are stable at about 25±5° C. for at least 12 months. In one embodiment, the pharmaceutical compositions are stable at about 5±5° C. for at least 24 months. In one embodiment, the pharmaceutical compositions are stable at about 25±5° C. for at least 24 months.

Methods of Use

Disclosed herein is a method of treating congenital adrenal hyperplasia (CAH) in a subject in need thereof, comprising administering a pharmaceutical composition comprising Compound 1, or a pharmaceutically acceptable salt or solvate thereof. In some embodiments, CAH is classic CAH. In some embodiments, CAH is non-classic CAH. In some embodiments, the methods described herein result in the reduction of a hormone level. Such hormones include deoxycorticosterone, 11-deoxycortisol, cortisol, corticosterone, aldosterone, pregnenolone, 17α-hydroxy pregnenolone, progesterone, 17α-hydroxy progesterone (17-OHP), dehydroepiandrosterone, androstenediol, androstenedione, testosterone, dihydrotestosterone, estrone, estradiol, estriol, and adrenocorticotropic hormone (ACTH). In some embodiments, the methods described herein result in the reduction of 17α-hydroxy progesterone (17-OHP). In some embodiments, the methods described herein result in the reduction of adrenocorticotropic hormone (ACTH), also known as corticotropin.

Also disclosed herein is a method of treating congenital adrenal hyperplasia (CAH) in a subject in need thereof, the method comprising:
(i) measuring a hormone level in the subject in need thereof,
(ii) administering Compound 1:

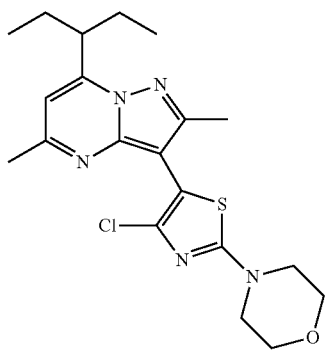 [SMILES: CCC(CC)c1cc(C)nc2c(-c3sc(N4CCOCC4)nc3Cl)c(C)nn12]

or a pharmaceutically acceptable salt or solvate thereof;
(iii) repeating steps (i) and (ii) until the hormone level reaches a pre-determined range followed by a maintenance therapy of a daily dosing of compound 1.

In some embodiment, the hormone is 17α-Hydroxyprogesterone (17-OHP), adrenocorticotropic hormone (ACTH), testosterone, or androstenedione.

In some embodiment, the hormone is 17-OHP, and the pre-determined range is from about 200 ng/dL to about 400 ng/dL. In some embodiment, the hormone is 17-OHP, and the pre-determined range is less than about 400 ng/dL, less than about 350 ng/dL, less than about 300 ng/dL, less than about 250 ng/dL, or less than about 200 ng/dL.

In some embodiment, the hormone is ACTH, and the pre-determined range is below about 100 pg/mL. In some embodiment, the hormone is ACTH, and the pre-determined range is below about 100 pg/mL, below about 90 pg/mL, or below about 80 pg/mL.

In some embodiment, the hormone is testosterone and the pre-determined range is from about 14 ng/dL to about 76 ng/dL. In some embodiment, the hormone is testosterone and the pre-determined range is less than about 76 ng/dL, less than about 70 ng/dL, less than about 65 ng/dL, less than about 60 ng/dL, less than about 55 ng/dL, less than about 50 ng/dL, less than about 45 ng/dL, less than about 40 ng/dL, less than about 35 ng/dL, less than about 30 ng/dL, less than about 25 ng/dL, less than about 20 ng/dL, or less than about 15 ng/dL.

In some embodiment, the hormone is androstenedione and the pre-determined range is from about 30 ng/dL to about 200 ng/dL in males. In some embodiment, the hormone is androstenedione and the pre-determined range is less than about 200 ng/dL, less than about 150 ng/dL, less than about 100 ng/dL, less than about 50 ng/dL, or less than about 30 ng/dL in males.

In some embodiment, the hormone is androstenedione and the pre-determined range is from about 40 ng/dL to about 150 ng/dL in females. In some embodiment, the hormone is androstenedione and the pre-determined range is less about 150 ng/dL, less about 100 ng/dL, less about 50 ng/dL, or less about 40 ng/dL in females.

In some embodiments, the methods described herein include administration of the pharmaceutical composition comprising Compound 1, or a pharmaceutically acceptable salt or solvate thereof once a month, twice a month, three times a month, once a week, twice a week, three times a week, once every two days, once a day, twice a day, three times a day, or four times a day. In some embodiments, the methods described herein administer Compound 1, or a pharmaceutically acceptable salt or solvate thereof once a day. In some embodiments, the methods described herein administer Compound 1, or a pharmaceutically acceptable salt or solvate thereof twice a day.

In some embodiments, the methods described herein include administration of about 1 mg to about 2000 mg of Compound 1, or a pharmaceutically acceptable salt or solvate thereof, per day. In some embodiments, Compound 1 is administered at a dose between about 50 mg/day and about 1600 mg/day. In some embodiments, Compound 1 is administered at a dose between about 50 mg/day and about 1500 mg/day. In some embodiments, Compound 1 is administered at a dose between about 50 mg/day and about 1400 mg/day. In some embodiments, Compound 1 is administered at a dose between about 50 mg/day and about 1300 mg/day. In some embodiments, Compound 1 is administered at a dose between about 50 mg/day and about 1200 mg/day. In some embodiments, Compound 1 is administered at a dose between about 50 mg/day and about 1100 mg/day. In some embodiments, Compound 1 is administered at a dose between about 50 mg/day and about 1000 mg/day. In some embodiments, Compound 1 is administered at a dose between about 50 mg/day and about 900 mg/day. In some embodiments, Compound 1 is administered at a dose between about 50 mg/day and about 800 mg/day. In some embodiments, Compound 1 is administered at a dose between about 60 mg/day and about 800 mg/day. In some embodiments, Compound 1 is administered at a dose between about 70 mg/day and about 800 mg/day. In some embodiments, Compound 1 is administered at a dose between about 80 mg/day and about 800 mg/day. In some embodiments, Compound 1 is administered at a dose between about 90 mg/day and about 800 mg/day. In some embodiments, Compound 1 is administered at a dose between about 100 mg/day and about 800 mg/day. In some embodiments, Compound 1 is administered at a dose between about 100 mg/day and about 700 mg/day. In some embodiments, Compound 1 is administered at a dose between about 100 mg/day and about 600 mg/day. In some embodiments, Compound 1 is administered at a dose between 150 mg/day and about 600 mg/day. In some embodiments, Compound 1 is administered at a dose between 200 mg/day and about 600 mg/day. In some embodiments, Compound 1 is administered at a dose between 200 mg/day and about 500 mg/day. In some embodiments, Compound 1 is administered at a dose between 200 mg/day and about 400 mg/day.

In some embodiments, Compound 1 is administered at a dose of about 500 mg/day. In some embodiments, Compound 1 is administered at a dose of about 400 mg/day. In some embodiments, Compound 1 is administered at a dose of about 300 mg/day. In some embodiments, Compound 1 is administered at a dose of about 200 mg/day. In some embodiments, Compound 1 is administered at a dose of about 100 mg/day.

In some embodiments, about 100 mg to about 1600 mg of Compound 1, or a pharmaceutically acceptable salt or solvate thereof, is administered per day. In some embodiments, about 200 mg to about 1600 mg of Compound 1, or a pharmaceutically acceptable salt or solvate thereof, is administered per day. In some embodiments, about 200 mg to about 1200 mg of Compound 1, or a pharmaceutically acceptable salt or solvate thereof, is administered per day. In some embodiments, about 200 mg to about 1000 mg of Compound 1, or a pharmaceutically acceptable salt or solvate thereof, is administered per day. In some embodiments, about 200 mg to about 800 mg of Compound 1, or a pharmaceutically acceptable salt or solvate thereof, is administered per day. In some embodiments, about 100 mg to about 800 mg of Compound 1, or a pharmaceutically acceptable salt or solvate thereof, is administered per day. In some embodiments, about 200 mg to about 800 mg of Compound 1, or a pharmaceutically acceptable salt or solvate thereof, is administered per day. In some embodiments, about 100 mg to about 600 mg of Compound 1, or a pharmaceutically acceptable salt or solvate thereof, is administered per day. In some embodiments, about 200 mg to about 600 mg of Compound 1, or a pharmaceutically acceptable salt or solvate thereof, is administered per day. In some embodiments, about 300 mg to about 600 mg of Compound 1, or a pharmaceutically acceptable salt or solvate thereof, is administered per day. In some embodiments, about 100 mg to about 400 mg of Compound 1, or a pharmaceutically acceptable salt or solvate thereof, is administered per day. In some embodiments, about 200 mg to about 400 mg of Compound 1, or a pharmaceutically acceptable salt or solvate thereof, is administered per day. In some embodiments, about 300 mg to about 400 mg of Compound 1, or a pharmaceutically acceptable salt or solvate thereof, is administered each day.

In some embodiments, less than about 2000 mg Compound 1, or a pharmaceutically acceptable salt or solvate thereof, is administered per day. In some embodiments, less than about 1800 mg Compound 1, or a pharmaceutically acceptable salt or solvate thereof, is administered per day. In some embodiments, less than about 1600 mg Compound 1, or a pharmaceutically acceptable salt or solvate thereof, is administered per day. In some embodiments, less than about 1400 mg Compound 1, or a pharmaceutically acceptable salt or solvate thereof, is administered per day. In some embodiments, less than about 1200 mg Compound 1, or a pharmaceutically acceptable salt or solvate thereof, is administered per day. In some embodiments, less than about 1000 mg Compound 1, or a pharmaceutically acceptable salt or solvate thereof, is administered per day. In some embodiments, less than about 800 mg Compound 1, or a pharmaceutically acceptable salt or solvate thereof, is administered per day. In some embodiments, less than about 600 mg Compound 1, or a pharmaceutically acceptable salt or solvate thereof, is administered per day. In some embodiments, less than about 500 mg Compound 1, or a pharmaceutically acceptable salt or solvate thereof, is administered per day. In some embodiments, less than about 400 mg Compound 1, or a pharmaceutically acceptable salt or solvate thereof, is administered per day. In some embodiments, less than about 300 mg Compound 1, or a pharmaceutically acceptable salt or solvate thereof, is administered per day. In some embodiments, less than about 200 mg Compound 1, or a pharmaceutically acceptable salt or solvate thereof, is administered per day.

In some embodiments, the methods described herein include administration of the pharmaceutical compositions described herein wherein the subject is in the fed state. In some embodiments, the methods described herein include administration of the pharmaceutical compositions described herein wherein the subject is in the fasted state.

In some embodiments, the methods described herein include administration of the pharmaceutical compositions described herein at bedtime.

In some embodiments, the methods described herein include administration of the pharmaceutical compositions described herein less than about 4 hours before sleep. In some embodiments, the methods described herein include administration of the pharmaceutical compositions described herein less than about 3 hours before sleep. In some embodiments, the methods described herein include administration of the pharmaceutical compositions described herein less than about 2 hours before sleep. In some embodiments, the methods described herein include administration of the pharmaceutical compositions described herein less than about 1 hour before sleep. In some embodiments, the methods described herein include administration of the pharmaceutical compositions described herein less than about 30 mins before sleep.

In some embodiments, the methods described herein include administration of the pharmaceutical compositions described herein in the evening.

In some embodiments, the methods described herein include administration of the pharmaceutical compositions described herein at about 11 pm at night. In some embodiments, the methods described herein include administration of the pharmaceutical compositions described herein at about 10 pm at night. In some embodiments, the methods described herein include administration of the pharmaceutical compositions described herein at about 9 pm at night. In some embodiments, the methods described herein include administration of the pharmaceutical compositions described herein at about 8 pm at night.

In some embodiments, the methods described herein include administration of the pharmaceutical compositions described herein at or before the expected circadian release of adrenocorticotropic hormone (ACTH). In some embodiments, the methods described herein include administration of the pharmaceutical compositions described herein about 3-4 hours before the expected circadian release of adrenocorticotropic hormone (ACTH). In some embodiments, the subject in need thereof is from about 12 years of age to about 20 years of age.

In one aspect, the present disclosure provides a method of improving hyperandrogenic symptoms in a subject in need thereof, comprising administering a pharmaceutical composition comprising Compound 1:

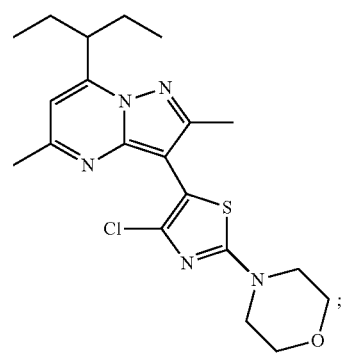 [SMILES: CCC(CC)c1cc(C)nc2c(-c3sc(N4CCOCC4)nc3Cl)c(C)nn12]

or a pharmaceutically acceptable salt or solvate thereof, wherein Compound 1 is administered at a dose between about 50 mg/day and about 1600 mg/day. In some embodiments, the hyperandrogenic symptoms are selected from the group consisting of acne, hirsutism and alopecia.

In one aspect, the present disclosure provides a method of treating menstrual irregularity, ovulatory dysfunction or infertility, in a subject in need thereof, comprising administering a pharmaceutical composition comprising Compound 1:

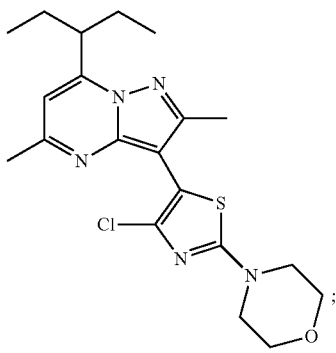 [SMILES: CCC(CC)c1cc(C)nc2c(-c3sc(N4CCOCC4)nc3Cl)c(C)nn12]

or a pharmaceutically acceptable salt or solvate thereof, wherein Compound is a ministered at a dose between about 50 mg/day and about 1600 mg/day.

In one aspect, the present disclosure provides a method of improving metabolic symptoms in a subject in need thereof, comprising administering a pharmaceutical composition comprising Compound 1:

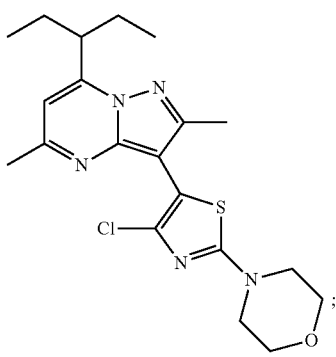 [SMILES: CCC(CC)c1cc(C)nc2c(-c3sc(N4CCOCC4)nc3Cl)c(C)nn12]

or a pharmaceutically acceptable salt or solvate thereof, wherein Compound 1 is administered at a dose between about 50 mg/day and about 1600 mg/day. In some embodiments, the metabolic symptoms are selected from the group consisting of body weight, BMI, waist circumference, blood pressure and glycemic control.

In one aspect, the present disclosure provides a method of improving quality of life in a subject in need thereof, comprising administering a pharmaceutical composition comprising Compound 1:

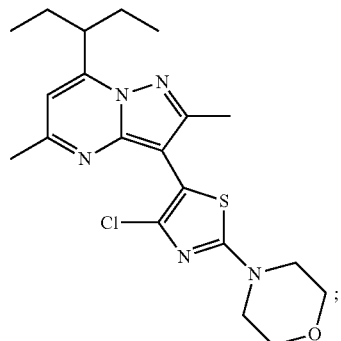

or a pharmaceutically acceptable salt or solvate thereof, wherein Compound 1 is administered at a dose between about 50 mg/day and about 1600 mg/day, wherein treatment results in an improved quality of life.

Combination Therapy

Disclosed herein is a method of treating congenital adrenal hyperplasia (CAH) in a subject in need thereof, comprising administering a combination of Compound 1, or a pharmaceutically acceptable salt or solvate thereof; and a glucocorticoid. In some embodiments, the amount of glucocorticoid administered is reduced as compared to a method not comprising administering Compound 1, or a pharmaceutically acceptable salt or solvate thereof.

In some embodiments, the methods described herein reduce the amount of a glucocorticoid administered from a supraphysiologic amount to a physiologic amount.

In some embodiments, the methods described herein reduce the symptoms associated with high-dose glucocorticoid therapy. In some embodiments, the symptoms associated with high-dose glucocorticoid therapy are obesity, insulin resistance, metabolic abnormalities, hypertension, cardiovascular diseases, or osteoporosis.

In some embodiments, the amount of glucocorticoid administered is reduced by about 5%, about 10%, about 15%, about 20%, about 25%, about 30%, about 35%, about 40%, about 45%, about 50%, about 55%, about 60%, about 65%, about 70%, about 80, or about 90% as compared to a method not comprising administering Compound 1, or a pharmaceutically acceptable salt or solvate thereof. In some embodiments, the amount of glucocorticoid administered is reduced by about 5%, about 10%, about 15%, about 20%, about 25%, about 30%, about 35%, about 40%, about 45%, about 50%, about 55%, or about 60% as compared to a method not comprising administering Compound 1, or a pharmaceutically acceptable salt or solvate thereof.

In some embodiments, the amount of glucocorticoid administered is reduced by about 1% to about 90%, about 1% to about 60%, about 1% to about 30%, about 1% to about 10%, about 10% to about 50%, about 10% to about 40%, about 10% to about 30%, about 15% to about 25%, about 20% to about 30%, about 5% to about 25%, about 20% to about 50%, about 30% to about 60%, or about 40% to about 70% as compared to a method not comprising administering Compound 1, or a pharmaceutically acceptable salt or solvate thereof.

In some embodiments, the glucocorticoid is administered at a dose between about 0.1 mg/day and about 25 mg/day. In some embodiments, the glucocorticoid is administered at a dose between about 1 mg/day and about 20 mg/day. In some embodiments, the glucocorticoid is administered at a dose between about 1 mg/day and about 15 mg/day. In some embodiments, the glucocorticoid is administered at a dose between about 1 mg/day and about 12 mg/day. In some embodiments, the glucocorticoid is administered at a dose between about 1 mg/day and about 11 mg/day. In some embodiments, the glucocorticoid is administered at a dose between about 1 mg/day and about 10 mg/day. In some embodiments, the glucocorticoid is administered at a dose between about 1 mg/day and about 9 mg/day. In some embodiments, the glucocorticoid is administered at a dose between about 1 mg/day and about 8 mg/day. In some embodiments, the glucocorticoid is administered at a dose between about 1 mg/day and about 7 mg/day. In some embodiments, the glucocorticoid is administered at a dose between about 1 mg/day and about 6 mg/day. In some embodiments, the glucocorticoid is administered at a dose between about 1 mg/day and about 5 mg/day. In some embodiments, the glucocorticoid is administered at a dose between about 1 mg/day and about 4 mg/day. In some embodiments, the glucocorticoid is administered at a dose between about 1 mg/day and about 3 mg/day. In some embodiments, the glucocorticoid is administered at a dose between about 1 mg/day and about 2 mg/day. In some embodiments, the glucocorticoid is administered at a dose between about 3 mg/day and about 13 mg/day. In some embodiments, the glucocorticoid is administered at a dose between about 5 mg/day and about 11 mg/day. In some embodiments, the glucocorticoid is administered at a dose between about 8 mg/day and about 11 mg/day. In some embodiments, the glucocorticoid is administered at a dose between about 9 mg/day and about 12 mg/day. In some embodiments, the glucocorticoid is administered at a dose between about 9 mg/day and about 10 mg/day. In some embodiments, the glucocorticoid is administered at a dose between about 5 mg/day and about 10 mg/day.

In some embodiments, Compound 1, or a pharmaceutically acceptable salt or solvate thereof, and the glucocorticoid are administered concurrently. In some embodiments, Compound 1, or a pharmaceutically acceptable salt or solvate thereof, and the glucocorticoid are administered in one pharmaceutical composition. In some embodiments, Compound 1, or a pharmaceutically acceptable salt or solvate thereof, and the glucocorticoid are administered concurrently in separate pharmaceutical compositions.

In some embodiments, Compound 1, or a pharmaceutically acceptable salt or solvate thereof, and the glucocorticoid are administered sequentially. In some embodiments, Compound 1, or a pharmaceutically acceptable salt or solvate thereof, and the glucocorticoid are administered within 24 hours. In some embodiments, Compound 1, or a pharmaceutically acceptable salt or solvate thereof, and the glucocorticoid are administered within 12 hours. In some embodiments, Compound 1, or a pharmaceutically acceptable salt or solvate thereof, and the glucocorticoid are administered within 8 hours. In some embodiments, Compound 1, or a pharmaceutically acceptable salt or solvate thereof, and the glucocorticoid are administered within 6 hours. In some embodiments, Compound 1, or a pharmaceutically acceptable salt or solvate thereof, and the glucocorticoid are administered within 4 hours. In some embodiments, Compound 1, or a pharmaceutically acceptable salt or solvate thereof, and the glucocorticoid are administered within 2 hours. In some embodiments, Compound 1, or a pharmaceutically acceptable salt or solvate thereof, and the glucocorticoid are administered within 1 hour. In some embodiments, Compound 1, or a pharmaceutically acceptable salt or solvate thereof, and the glucocorticoid are administered within 30 minutes. In some embodiments, Compound 1, or a pharmaceutically acceptable salt or solvate thereof, and the glucocorticoid are administered within 10 minutes.

In some embodiments, the glucocorticoid is beclomethasone, betamethasone, budesonide, cortisone, dexamethasone, hydrocortisone, methylprednisolone, prednisolone, prednisone, or triamcinolone. In some embodiments, the glucocorticoid is hydrocortisone.

In some embodiments, the glucocorticoid is hydrocortisone and the dose administered is less than the recommended dose of 15-25 mg/day.

In some embodiments, the glucocorticoid is prednisone and the dose administered is less than the recommended dose of 5-7.5 mg/day.

In some embodiments, the glucocorticoid is prednisolone and the dose administered is less than the recommended dose of 4-6 mg/day.

In some embodiments, the glucocorticoid is dexamethasone and the dose administered is less than the recommended dose of 0.25-0.5 mg/day.

Disclosed herein is a method of treating congenital adrenal hyperplasia (CAH) in a subject in need thereof, comprising administering a combination of Compound 1, or a pharmaceutically acceptable salt or solvate thereof; a glucocorticoid; and optionally a mineralcorticoid. In some embodiments, the mineralocorticoid is fludrocortisone and the dose is less than the recommended dose of 0.05-0.2 mg/day.

EXAMPLES

The following examples further illustrate the invention but should not be construed as in any way limiting its scope. In particular, the processing conditions are merely exemplary and can be readily varied by one of ordinary skill in the art.

All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Unless defined otherwise, technical and scientific terms used herein have the same meaning as is commonly understood by one of skill in the art to which this invention belongs.

Example 1: Pharmaceutical Composition

The pharmaceutical composition is manufactured as size 1 white hard gelatin capsules containing 200 mg of Compound 1 micronized to and average size of 10 microns or less. The pharmaceutical composition contains no additional excipients.

Example 2: Stability of the Pharmaceutical Composition

Stability Data Summary

A summary of the pharmaceutical composition stability studies is provided in Table 1. The pharmaceutical composition is a Compound 1 neat-filled into size 0 capsules with no added excipients, in 3 strength configurations: 1-mg, 5-mg, and 50-mg. The capsules were blister packaged in a polyvinyl chloride (PVC)-based film.

Under long term and accelerated conditions, no significant trend was observed in the three lots for any of the attributes evaluated throughout the course of the stability study.

TABLE 1

Summary of Stability

| Lot Number | Strength | CCS | Stability Conditions | Available Data |
|---|---|---|---|---|
| #1 | 1-mg | PVC-based blister pack | 25° C./60% RH 40° C./75% RH | 6 months 6 months |
| #2 | 5-mg | PVC-based blister pack | 25° C./60% RH 40° C./75% RH | 6 months 6 months |
| #3 | 50-mg | PVC-based blister pack | 25° C./60% RH 40° C./75% RH | 6 months 6 months |
| #4 | 200-mg | 75 mL HDPE bottle | 25° C./60% RH 40° C./75% RH | 1 month 9 months |
| #5 | 200-mg | 30 mL HDPE bottle | 25° C./60% RH 40° C./75% RH | 6 months 6 months |
| #6 | 200-mg | 30 mL HDPE bottle | 25° C./60% RH 40° C./75% RH | 6 months 6 months |

CCS = container closure system;
CRC = child-resistant closure;
DoM = date of manufacture;
HDPE = high density polyethylene;
PVC = polyvinyl chloride Stability Protocols The stability protocol for various pharmaceutical compositions is provided in Table 2, 3, and 4.

TABLE 2

Stability Protocol

| | | | Time (months) | | |
|---|---|---|---|---|---|
| Test | Acceptance Criteria | $T_0$ | 1 | 3 | 6 |
| Appearance | Size 0 blue capsule containing yellow powder, blister pack and foil backing intact | X | A, B | A, B | A, B |
| Assay | Report (% Label Claim) | X | A, B | A, B | A, B |
| Related Substances | Report RRT and % each individual species and total | X | A, B | A, B | A, B |
| Disintegration | Report | X | A, B | A, B | A, B |

RRT = relative retention time
X-testing performed at the time study was initiated
A-samples stored under long term conditions of 25 ± 2° C./60 ± 5% RH
B-samples stored under accelerated conditions of 40 ± 2° C./75 ± 5% RH

TABLE 3

Stability Protocol (200-mg capsules in 30 mL HDPE bottles)

| | | | Time (months) | | |
|---|---|---|---|---|---|
| Test | Acceptance Criteria | $T_0$ | 1 | 3 | 6 |
| Appearance | Size 1 white capsule containing an off-white to yellow powder | X | A, B | A, B | A, B |
| Assay (% LC) | 90.0-110.0 | X | A, B | A, B | A, B |
| Related Substances | | | | | |
| Any Unspecified Impurity (%) | ≤1.0 | X | A, B | A, B | A, B |
| Total Impurities (%) | ≤2.0 | | | | |

TABLE 3-continued

Stability Protocol (200-mg capsules in 30 mL HDPE bottles)

| | | | Time (months) | | |
|---|---|---|---|---|---|
| Test | Acceptance Criteria | $T_0$ | 1 | 3 | 6 |
| Disintegration (min) | NMT 15 | X | A, B | A, B | A, B |
| Water Activity | Report result | X | A, B | A, B | A, B |

LC = label claim;
NMT = not more than
X-testing performed at the time study was initiated
A-samples stored under long term conditions of 25 ± 2° C./60 ± 5 % RH
B-samples stored under accelerated conditions of 40 ± 2° C./75 ± 5 % RH

TABLE 4

Stability Protocol (200-mg capsules in 30 mL HDPE bottles) for Lots to be Used in Phase 2 Clinical Study

| | | | Time (months) | | | | |
|---|---|---|---|---|---|---|---|
| Test | Acceptance Criteria | $T_0$ | 1 | 3 | 6 | 9 | 12 |
| Appearance | Size 1 white capsule containing an off-white to yellow powder | X | B | A, B | A, B | A | A |
| Assay (% LC) | 90.0-110.0 | X | B | A, B | A, B | A | A |
| Related Substances | ≤1.0 | X | B | A, B | A, B | A | A |
| Any Unspecified Impurity (%) | ≤2.0 | | | | | | |
| Total Impurities (%) | | | | | | | |
| Disintegration (min) | NMT 15 | X | B | A, B | A, B | A | A |
| Water Activity | Report result | X | n/a | n/a | n/a | A | A |
| Microbial Enumeration Total Aerobic Microbial Count (CFU/g) | NMT 2000 CFU/g | X | n/a | n/a | n/a | A | A |
| Total Combined Yeast and Mold (CFU/g) Count | NMT 200 CFU/g | | | | | | |
| Test for Specified Microorganisms E. coli (/g) | Absent | X | n/a | n/a | n/a | A | A |

CFU = colony forming units; LC = label claim; n/a = not applicable; NMT = not more than
X-testing performed at the time study was initiated
A-samples stored under long term conditions of 25 ± 2° C./60 ± 5% RH
B-samples stored under accelerated conditions of 40 ± 2° C./75 ± 5% RH The supportive data demonstrate that the pharmaceutical composition is stable for a minimum of 6 months (end of study). No adverse trends were observed under long term and accelerated conditions. The assay results were consistent through the entire study and no new related substances species were observed during the stability study. The reported stability results for lots stored in a blister packaging configuration are considered supportive for the updated packaging configuration of a 30-mL HDPE bottle, induction seal, and a child resistant cap. There are no excipients in either configuration and both configurations provide protection from light.

Example 3: Phase 1 Clinical Studies

Compound 1 has been investigated in 2 Phase 1 studies in healthy adult volunteers.

Study 1 was the first-in-human study that investigated the safety, tolerability, and PK of single-escalating doses of Compound 1, given orally, to healthy adult subjects. Safety and tolerability assessments were made over a wide range of single oral doses, and dose escalation did not proceed until safety data from the preceding doses had been reviewed. The data from this study were used for the selection of doses for Study 2.

The 2-part multiple-dose study, Study 2, determined the safety and tolerability of repeated daily doses of Compound 1 and investigated the effects on biomarkers of relevance for the treatment of alcohol dependence. Part B investigated the interaction of Compound 1 with midazolam (a cytochrome P450 3A4 [CYP3A4] substrate), determining whether Compound 1 significantly inhibited the metabolism of drugs that are metabolized by CYP3A4.

In Study 1, Compound 1 was administered to healthy adult subjects as a single PO dose of 2, 10, 50, 150, 400, or 800 mg in the fed state and 150 mg in the fasted state. Absorption occurred moderately late, achieving peak $C_{max}$ between 4 to 6 hours following dosing in the fed state.

Table 5 provides a summary of the PK parameters at each dose level. When Compound 1 was given in the fed state, median time to reach maximum plasma concentration ($T_{max}$) occurred between 4 and 6 hours. The median $T_{max}$ was 10.05 hours when Compound 1 was given in the fasted state at 150 mg and ranged between 6 and 12 hours, suggesting possible delayed absorption in the fasted state. Mean half-life ($t_{1/2}$) after a single PO dose (fed and fasted state) was between 31 and 44 hours, ranging from 11 to 101 hours. Apparent volume of distribution ($V_z/F$) was large and appeared highly variable with greatest variability observed at the 2 highest dose levels of 400 mg and 800 mg.

As part of this single-dose escalation study, a food effect PK investigation was performed to examine Compound 1 exposures in both the fed and fasted states at the 150-mg dose level. A total of 6 subjects were administered 150 mg Compound 1 in each of these 2 dosing groups. Of these 6 subjects, 4 subjects received Compound 1 at the same dose in both fed and fasted states. The administration of Compound 1 in the fasted state resulted in a much flatter mean concentration-time (i.e., with significantly lower absorption) profile when compared against the mean profile at the same dose, given within 5 minutes after a standardized breakfast meal. The mean $AUC_{0-\infty}$, and $C_{max}$ values for a 150-mg dose in the fed state was approximately 3- and 11-fold greater than that of the fasted state, respectively. Table 6 provides a summary of the PK parameters at the 150-mg dose level under both fed and fasted state conditions.

TABLE 6

Summary of Pharmacokinetic Parameters of Compound 1 Following Single Oral Dose Administration in Healthy Volunteers - Fed vs. Fasted State

| Pharmacokinetic Parameters | Geometric Mean (CV %) Analyte = Plasma Compound 1 | |
|---|---|---|
| | 150 mg Fed | 150 mg Fasted |
| N | 6 | 6 |
| $C_{max}$ (ng/ml) | 93.4 | 8.22 |

TABLE 5

Summary of Pharmacokinetic Parameters of Compound 1 Following Single Oral Dose Administration in Healthy Volunteers (all Fed)

| PK Parameters | Geometric Mean (CV %) Analyte = Plasma Compound 1 | | | | | |
|---|---|---|---|---|---|---|
| | 2 mg | 10 mg | 50 mg | 150 mg | 400 mg | 800 mg |
| N | 6 | 6 | 6 | 6 | 6 | 6 |
| $C_{max}$ (ng/mL) | 0.867 | 3.01 | 19.5 | 93.4 | 207 | 382 |
| | (53) | (87) | (39) | (22) | (92) | (110) |
| $T_{max}{}^a$ (h) max | 6.00 (4.00-6.00) | 4.00 (2.00-6.00) | 4.00 (3.00-6.00) | 4.00 (3.00-6.00) | 4.00 (3.00-6.00) | 6.00 (4.00-6.00) |
| $t_{1/2}{}^b$ (h) | NC (NC) | NC (NC) | 31 (10.8-53.4) | 29.2 (20.0-41.5) | 44.2 (20.2-101) | 41.9 (24.1-67.8) |
| $AUC_{0-t_{last}}$ (ng·h/mL) | NC (NC) | NC (NC) | 152 (60) | 891 (26) | 2300 (103) | 4390 (100) |
| $AUC_{0-\infty}$ (ng·h/mL) | NC (NC) | NC (NC) | 165 (64) | 956 (25) | 2580 (93) | 4850 (95) |
| CL/F (L/h) | NC (NC) | NC (NC) | 302 (64) | 157 (25) | 155 (93) | 165 (95) |
| $V_z/F$ (L) | NC (NC) | NC (NC) | 13500 (45) | 6620 (38) | 9890 (212) | 9970 (144) |
| $V_{ss}/F$ (L) | NC (NC) | NC (NC) | 8080 (36) | 4600 (33) | 6580 (152) | 6820 (120) |

AUC = area under the plasma concentration-time curve; CL/F = oral clearance; $C_{max}$ = maximum plasma concentration; CV = coefficient of variation; NC = not calculable; $t_{1/2}$ = elimination half-life; $T_{max}$ = time to reach maximum plasma concentration; $V_{ss}/F$ = volume of distribution at steady state; $V_z/F$ = volume of distribution at terminal phase $^a$ Median (range)

$^b$ Geometric mean (range)

TABLE 6-continued

Summary of Pharmacokinetic Parameters of Compound 1
Following Single Oral Dose Administration
in Healthy Volunteers - Fed vs. Fasted State

| Pharmacokinetic Parameters | Geometric Mean (CV %) Analyte = Plasma Compound 1 | |
|---|---|---|
| | 150 mg Fed | 150 mg Fasted |
| | (22) | (83) |
| $T_{max}{}^a$ (h) | 4.00 | 10.05 |
| | (3.00-6.00) | (6.00-12.00) |
| $t_{1/2}{}^b$ (h) | 29.2 | 38.4 |
| | (20.0-41.5) | (24.2-88.5) |
| $AUC_{0-t_{last}}$ (ng · h/mL) | 891 | 288 |
| | (26) | (48) |
| $AUC_{0-\infty}$ (ng · h/mL) | 956 | 331 |
| | (25) | (44) |
| CL/F (L/h) | 157 | 454 |
| | (25) | (44) |
| $V_z/F$ (L) | 6620 | 25100 |
| | (38) | (81) |
| $V_{ss}/F$ (L) | 4600 | 25200 |
| | (33) | (68) |

AUC = area under the plasma concentration-time curve; CL/F = apparent total body clearance; $C_{max}$ = maximum plasma concentration; CV = coefficient of variation; N = number of subjects; NC = not calculable; PK = pharmacokinetic; $T_{max}$ = time to reach maximum plasma concentration; $t_{1/2}$ = elimination half-life; $V_{ss}F$ = apparent volume of distribution at steady state during the terminal phase after extravascular administration; $V_z/F$ = apparent volume of distribution during the terminal phase after extravascular administration.
[a]Median (range)
[b]Geometric mean (range)

PK parameters $AUC_{0-\infty}$ and $C_{max}$ were analyzed separately for dose proportionality for Compound 1 from 50 to 800 mg when administered in the fed state. The analysis results suggested that for every doubling of dose, $AUC_{0-\infty}$ can be expected to increase 1.74 times more than what would be expected under dose proportionality. $C_{max}$ appeared more than dose proportional but the formal test was inconclusive as the 90% confidence interval were partially within the 0.8-1.25 interval. Dose proportionality across administered doses in the fed state could not be concluded on the basis of $AUC_{0-\infty}$ or $C_{max}$.

PK were also evaluated in the multiple-dose, dose-escalation study, Study 2. In Part A of the study, subjects were divided into 3 cohorts and received 50, 150, or 200 mg Compound 1 or placebo for 14 consecutive days (at least 6 subjects received Compound 1 and 2 subjects received placebo in each cohort). Blood concentrations of Compound 1 were close to steady-state levels after 2 weeks of dosing and the accumulation ratio was between 2.51 to 3.65. Part B investigated the interaction of Compound 1 with midazolam (a CYP3A4 substrate), thereby determining whether this compound significantly inhibited the metabolism of drugs that are metabolized by CYP3A4 serial blood samples were collected to determine plasma concentrations of study drug after a single dose of Compound 1 had been administered and at steady state. All dosing occurred in the fed state. An assessment of diurnal cortisol levels, plus when under conditions of glucose clamp, were also carried out both prior to and during the dosing period.

Overall concentration time profiles of Compound 1 showed that absorption was moderately delayed with $C_{max}$ achieved at a median of 5 hours following oral dosing. Consistent with the single-dose study (Study 1), concentrations appeared to decline in a bi-exponential manner, characterized by a rapid decrease within the first 24 hours. Following multiple daily dosing for 2 weeks, the $t_{1/2}$ of Compound 1 exceeded 100 hours; therefore, an accumulation ratio of Compound 1 was between 2.51 to 3.65 (see Table 7). The $T_{max}$ appeared to be consistent across doses. Overall half-lives, weight normalized CL/F and V/F were consistent for 150 and 200 mg. However, the values for these latter 2 parameters were almost doubled at the 50-mg dose level. Variability (CV %) for apparent clearance and volume of distribution were large and not reduced with weight-normalization.

TABLE 7

Summary of Noncompartmental Pharmacokinetic Parameters of Compound 1
After Single (Day 1) and Multiple (Day 14) Oral Doses of 50 mg, 150 mg, and 200 mg of
Compound 1 in Part A of the Study

| | Geometric Mean (CV %) | | | | | |
|---|---|---|---|---|---|---|
| | 50 mg Day 1 | 150 mg Day 1 | 200 mg Day 1 | 50 mg Day 14 | 150 mg Day 14 | 200 mg Day 14 |
| N | 8 | 9 | 7 | 8 | 9 | 6 |
| $C_{max}$ (ng/ml) | 22.7 | 127 | 143 | 50.3 | 222 | 314 |
| | (59) | (52) | (62) | (56) | (58) | (93) |
| $T_{max}{}^a$ (hr) | 4.52 | 5.00 | 5.00 | 5.00 | 5.00 | 5.00 |
| | (3.00-0.00) | (5.00-6.00) | (2.00-5.00) | (3.00-5.00) | (3.00-5.03) | (3.00-5.00) |
| Effective $t_{1/2}{}^b$ (hr) | NC | NC | NC | 37.7 | 32.7 | 52.0 |
| | NC | NC | NC | (27.4) | (29.7) | |
| $AUC_{0-\infty}$ (ng · hr/mL) | NC | NC | NC | 980 | 4680 | 5660 |
| | NC | NC | NC | (53.8) | (104) | (122) |
| $AUC_{0-24 h}$ (ng · hr/mL) | 97.6 | 590 | 559 | 273 | 1480 | 2040 |
| | (58) | (56) | (55[c]) | (56) | (66) | (98) |
| $C_{avg}$ (ng/mL) | NC | NC | NC | 11.4 | 61.7 | 85.0 |
| | NC | NC | NC | (56) | (66) | (98) |
| $CL_{ad}/F$ (L/hr) | NC | NC | NC | 183 | 101 | 98 |
| | NC | NC | NC | (56) | (66) | (98) |
| | | | WT-norm | | | |
| $Cl_{ad}/F$ (L/hr/kg) | NC | NC | NC | 2.88 | 1.42 | 1.50 |
| | NC | NC | NC | (46.9) | (72.9) | (89.9) |
| Vz/F (L) | NC | NC | NC | 33500 | 17600 | 16300 |
| | NC | NC | NC | (90) | (59) | (76) |

TABLE 7-continued

Summary of Noncompartmental Pharmacokinetic Parameters of Compound 1
After Single (Day 1) and Multiple (Day 14) Oral Doses of 50 mg, 150 mg, and 200 mg of
Compound 1 in Part A of the Study

|  | Geometric Mean (CV %) | | | | | |
| --- | --- | --- | --- | --- | --- | --- |
|  | 50 mg Day 1 | 150 mg Day 1 | 200 mg Day 1 | 50 mg Day 14 | 150 mg Day 14 | 200 mg Day 14 |
| Vss/F (L) | NC | NC | NC | 12900 | 6170 | 5080 |
|  | NC | NC | NC | (91) | (40) | (78) |
|  |  |  | WT-norm |  |  |  |
| Vss/F (L/kg) | NC | NC | NC | 204 | 86.5 | 77.4 |
|  | NC | NC | NC | (71.3) | (41.0) | (68.6) |
|  | NC | NC | NC | 2.80 | 2.51 | 3.65 |
| $R_A$ | NC | NC | NC | (27.4) | (29.7) | (34.4) |

AUC = area under the plasma concentration-time curve; CL/F = apparent clearance; $C_{max}$ = maximum plasma concentration; RA = accumulation ratio calculated as Day 14 $AUC_{0-24}$/Day 1 $AUC_{0-24}$; $t^{1/2}$ = terminal half-life; effective $t^{1/2}$ = half-life calculated by accumulation ratio; Tmax = time to maximum plasma concentration; Vss/F = volume of distribution at steady state; Vz/F = volume of distribution at terminal phase; WT-norm = weight normalized
[a] Median (range).
[b] Geometric mean (range).
[c] n = 6, Dropout Subject 306 not included in the calculation of summary statistics.

Table 8 presents the results of the dose proportionality assessment for the $AUC_{0-24}$ and $C_{max}$ over the tested dose range. For $AUC_{0-24}$ and $C_{max}$, the adjusted mean slope at Day 1 and Day 14 were all above the value of 1, suggesting a slightly more than proportional increase of $AUC_{0-24}$ and $C_{max}$ values with increasing doses.

TABLE 8

Summary of Assessment of Dose Proportionality as Assessed by the Power Model for Plasma Compound 1

| Parameter | Day | Mean Slope | Standard Error | 90% CI for Slope | CV % |
| --- | --- | --- | --- | --- | --- |
| $AUC_{0-24}$ (ng hr/mL) | 1 | 1.40 | 0.194 | (1.069, 1.737) | 59.3 |
|  | 14 | 1.48 | 0.221 | (1.104, 1.864) | 69.1 |
| $C_{max}$ (ng/ml) | 1 | 1.41 | 0.185 | (1.092, 1.728) | 57.5 |
|  | 14 | 1.33 | 0.210 | (0.972, 1.693) | 64.8 |

AUC = area under the plasma concentration-time curve;
$C_{max}$ = maximum plasma concentration Safety The safety of Compound 1 was evaluated in 2 Phase 1 studies in healthy adult volunteers (Study 1 and Study 2). In both studies, adverse events (AEs), clinical laboratory tests, vital signs (supine blood pressure and pulse rate), and electrocardiograms (ECGs) were evaluated. Overall, in Study 1, Compound 1 was well-tolerated.

Compound 1, when administered as multiple doses up to 200 mg, was generally well tolerated in the healthy subject population studied. In Study 1, the effects upon biomarkers of relevance for the treatment of alcohol dependence were investigated. Five clusters of an Addiction Research Center Inventory Questionnaire (ARCI-49) were used to compare the effect of Compound 1 vs. placebo: Morphine-Benzedrine Group Scale measuring euphoria; Lysergic-Acid-Diethyl-amide Group Scale estimating dysphoric and somatic changes; Pentobarbital-Chlorpromazine-Alcohol Group Scale measuring sedation; Benzedrine Group (BG) Scale measuring intellectual efficiency and energy; Amphetamine Group Scale measuring effects of d-amphetamine, respectively. No systematic pattern or dose-response for the change from baseline or for the difference over placebo in each cluster was observed.

In summary, single, oral doses up to 800 mg and multiple doses up to 200 mg of Compound 1 were well-tolerated by healthy male and female subjects.

Example 4: Phase 2 Clinical Studies

Cohort A of the Phase 2 Study includes a 6-week, multiple-dose, dose escalation study of Compound 1 for the treatment of adults with classic CAH. After screening, eligible patients will be enrolled into a 6-week treatment period followed by a 4-week washout/safety follow-up period.

This cohort will be conducted in approximately 9 patients, who will receive Compound 1 daily for up to 6 weeks. Compound 1 will be administered as an oral daily dose. Patients will undergo titration of Compound 1 through three escalating dosage strengths at 2-week intervals. Patients will have overnight PK/PD assessments performed at baseline, which include an pre-dose overnight assessment and a post-dose overnight assessment for PK/PD following administration of the first dose. At the end of each 2-week dosing period, patients will return for single overnight visits for steady-state PK/PD assessments. A follow-up outpatient visit will occur 30 days after their last dose. Upon completion of the initial cohort (Cohort A), the study will proceed to a multiple ascending dose (MAD) design with up to 3 sequential cohorts (Cohorts B, C, and D) to further evaluate the safety, PK, and PD of various SPR001 dosing regimens and to identify an optimal dose regimen. Each cohort will undergo a 2-week run-in period, a 2-week treatment period, and a 30-day washout and safety follow-up period. During the run-in period, which will occur during screening, subjects will document in a paper diary each dose of glucocorticoid medication taken, the time of each meal, and the time they went to bed and woke up each day, to ensure compliance with background glucocorticoid regimens and the stability of their daily routine.

Patients in Cohort B will receive study drug at 200 mg BID, with a dose in the morning and a dose in the evening, either with a meal or consumption of a standardized snack. For Cohorts C and D, the dose level and the frequency and timing of dosing will be determined based on interim data from the previous cohorts. However, the dose level of each successive cohort will be capped at twice the daily dose level of the previous cohort.

Study Design
  Study Type: Interventional
  Primary Purpose: Treatment
  Study Phase: Phase 2
  Interventional Study Model: Sequential Assignment
  Number of Cohorts: Up to 4
  Masking: No masking
  Allocation: Non-Randomized
  Enrollment: Up to approximately 27 [Anticipated]

| Arms and Interventions | |
|---|---|
| Arms | Assigned Interventions |
| Experimental: Cohort A<br>The first cohort of 9 patients will be administered Compound 1 at dose strength of 200 mg daily for 2 weeks, and escalating through 600 mg per day for 2 weeks and 1,000 mg per day for 2 weeks. | Drug: Compound 1<br>200-mg capsules |
| Experimental: Cohort B<br>Cohort B patients will be administered Compound 1 at a dose strength of 200 mg twice daily (BID) for 2 weeks. | Drug: Compound 1<br>200-mg capsules |
| Experimental: Cohort C<br>The dose/dose regimen for Cohort C will be determined based on an interim review of safety and PK/PD data from the previous Cohorts | Drug: Compound 1<br>50-mg or 200 mg capsules |
| Experimental: Cohort D<br>The dose/dose regimen for Cohort C will be determined based on an interim review of safety and PK/PD data from the previous Cohorts | Drug: Compound 1<br>50-mg or 200 mg capsules |

Outcome Measures
Primary Outcome Measure:
  1. To evaluate the safety of Compound 1 in subjects with CAH.
  2. To assess the efficacy of Compound 1 in subjects with classic CAH as measured by percent and absolute change in 17-OHP compared to baseline.
Secondary Outcome Measure:
  3. To explore the dose(s) of Compound 1 that cause pharmacodynamics changes in plasma concentrations of ACTH, androstenedione, and testosterone, as measured by the absolute and percent change from baseline by dose.
  4. To determine pharmacokinetics of Compound 1 in subjects with CAH.
  5. To explore potential relationships between pharmacodynamics and pharmacokinetics.
Exploratory
  6. To explore the dose(s) of Compound 1 that cause changes in pharmacodynamics biomarkers in urine, as measured by the absolute and percent change from baseline by dose.
Eligibility
  Minimum Age: 18 Years
  Maximum Age:
  Sex: All
  Gender Based: No
  Accepts Healthy Volunteers: No
  Criteria: Inclusion Criteria:
Inclusion Criteria:
  Male and female patients age 18 or older.
  Documented diagnosis of classic CAH due to 21-hydroxylase deficiency
  Elevated 17-OHP at screening
  On a stable glucocorticoid replacement regimen for a minimum of 30 days
Exclusion Criteria:
  Clinically significant unstable medical condition, illness, or chronic disease
  Clinically significant psychiatric disorder.
  Clinically significant abnormal laboratory finding or assessment
  History of bilateral adrenalectomy or hypopituitarism
  Pregnant or nursing females
  Use of any other investigational drug within 30 days
  Unable to understand and comply with the study procedures, understand the risks, and/or unwilling to provide written informed consent.

Results:
The phase 2 study showed that Compound 1 was generally well-tolerated. The study established a range of safe doses after exploring a wide range of doses (5-fold range) (see FIG. 1).

Figure 2:
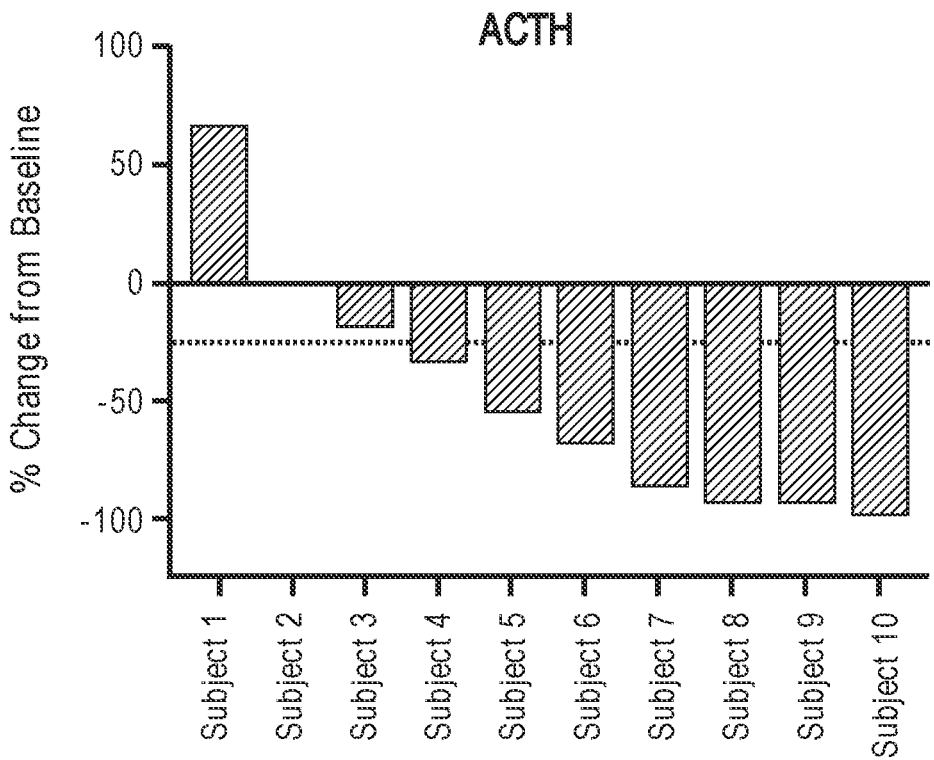
FIG. 2 demonstrates the attenuation of ACTH across different subjects due to the administration of Compound 1.

With respect to patient-level response to Compound 1, 80% showed reduced ACTH (see FIG. 2). Generally, attenuation of ACTH demonstrates target engagement and functional $CRF_1$ receptor antagonism. 80% of patient subjects demonstrated reduction in ACTH. 70% of subject demonstrated more than 25% reduction in ACTH. 40% of subjects were in the normal range after treatment.

Figure 3:
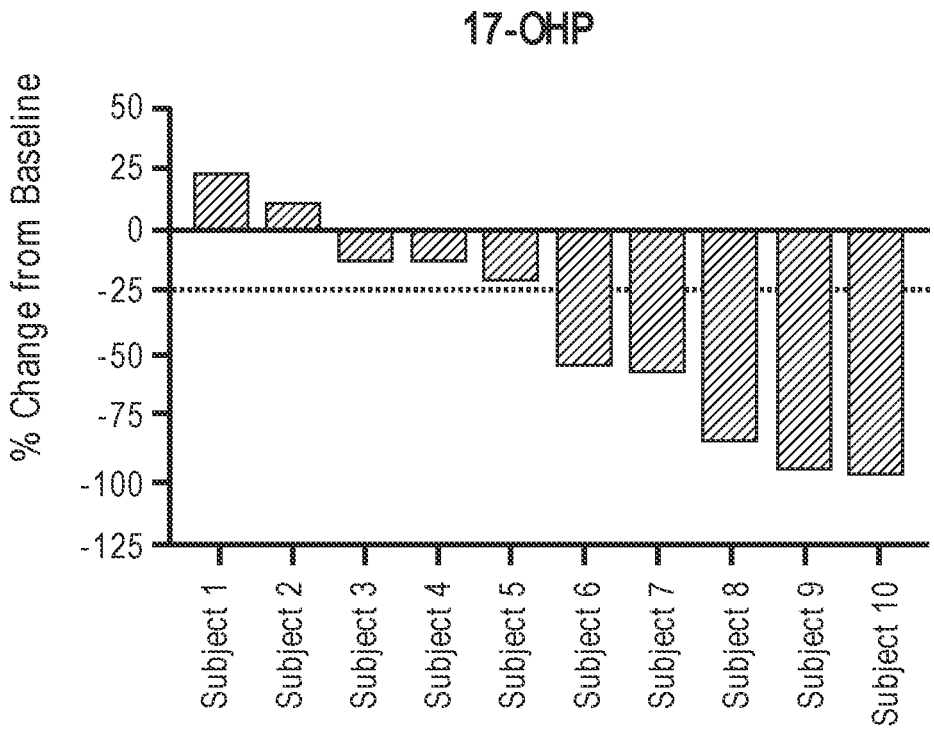
FIG. 3 demonstrates the reduction in 17-OHP due to the administration of Compound 1.

A reduction of 17-OHP demonstrates "control" of the disease based on Standard guidelines. This allows for steroid taper. 80% of subjects demonstrated reduction in 17-OHP (see FIG. 3). 50% of subjects demonstrated more than 25% reduction in 17-OHP. 50% of subjects were within the guideline range (1200 ng/dL) after treatment.

Figure 4:
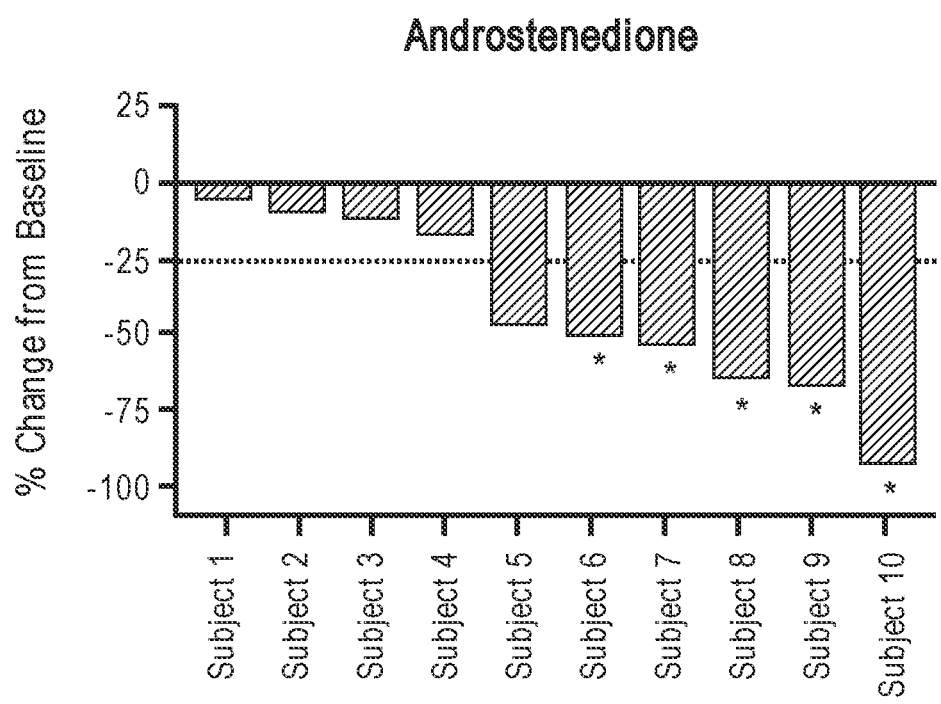
FIG. 4 demonstrates the reduction of Androstenedione due to the administration of Compound.

Compound 1 attenuates morning rise in A4 which indicates an ability to control excess androgen production and associated symptoms (see FIG. 4). 100% of subjects demonstrated reduction in Androstenedione (at various doses). 60% of subjects demonstrated more than 25% reduction in Androstenedione. 50% of subjects were within normal reference range after treatment.

Example 5: 3-Month Phase 2 Study

This is a 3-month Phase 2 study to evaluate the safety and efficacy of Compound 1 in subjects with classic CAH. This study will investigate the extended use of Compound 1 over a 3-month period in combination with replacement glucocorticoids and mineralocorticoids in the treatment of CAH.

This study will enroll up to approximately 24 eligible subjects who will receive Compound 1 daily for up to 3-months. Compound 1 will be administered as an oral daily dose. At the end of each 2-week dosing period, patients will return for morning laboratory assessments. A follow-up outpatient visit will occur 30 days after their last dose.

Study Design
- Study Type: Interventional
- Primary Purpose: Treatment
- Study Phase: Phase 2
- Interventional Study Model: Sequential Assignment
- Number of Arms: 1
- Masking: No Masking
- Allocation: Non-Randomized
- Enrollment: Up to approximately 24 [anticipated]

Outcome Measures
Primary Outcome Measure:
1. To evaluate the safety of Compound 1 in subjects with CAH.

Second Outcome Measure:
2. To evaluate the efficacy of Compound 1 in subjects with CAH in terms of changes in hormones.

Exploratory:
3. To evaluate the effect of Compound 1 on quality of life, metabolic parameters, exploratory adrenal hormones, and semen analysis in subjects with CAH.

Eligibility:
- Minimum Age: 18 Years
- Maximum Age:
- Sex: All
- Gender Based: No
- Accepts Healthy Volunteers: No
- Criteria: Inclusion Criteria:
Inclusion Criteria:
- Male and female patients age 18 or older.
- Documented diagnosis of classic CAH due to 21-hydroxylase deficiency
- Elevated 17-OHP at screening
- On a stable glucocorticoid replacement regimen for a minimum of 30 days Exclusion Criteria:
- Clinically significant unstable medical condition, illness, or chronic disease
- Clinically significant psychiatric disorder.
- Clinically significant abnormal laboratory finding or assessment
- History of bilateral adrenalectomy or hypopituitarism
- Pregnant or nursing females
- Use of any other investigational drug within 30 days
- Unable to understand and comply with the study procedures, understand the risks, and/or unwilling to provide written informed consent.

Example 6: Adolescent Study

This is a Phase 2, open-label, multiple-dose study designed to provide proof of concept for the use of Compound 1 to treat adolescents 12 to 17 years of age with classic CAH. The study will evaluate the safety, efficacy, and PK of 2 weeks of treatment with Compound 1. Each subject will undergo a 2-week diary run-in period during screening, a 2-week treatment period, and a 30-day washout and safety follow-up period.

An adaptive design with up to 3 sequential dose cohorts (Cohorts 1, 2, and 3) is planned to identify an optimal dose strength and regimen in adolescents with classic CAH. Each cohort will initially enroll 3 subjects and may later enroll 3 more subjects based on interim data from the first 3 subjects, for a total of 6 subjects per cohort. However, if safety, efficacy, and PK results from 6 subjects are inconclusive, a cohort may be expanded up to a maximum of 12 subjects. Cohort 1 will receive study drug at 200 mg QD. Cohorts 2 and 3 will be sequentially activated only if further investigation of an optimal dose strength or regimen is required; the dose strength and frequency and timing of dosing for these cohorts will be determined based on interim data from the previous cohort(s). However, the dose strength administered to each successive cohort will be capped at twice the daily dose strength administered to the previous cohort.

This study will enroll patients with inadequately controlled CAH despite an existing glucocorticoid (GC) regimen (including any currently-available regimen: hydrocortisone, prednisone/prednisolone, and/or dexamethasone). In practice, CAH patients are typically treated with supraphysiologic doses of GCs which are both toxic and not effective in many adolescent patients. In this population, GCs are associated with multiple well-described short- and long-term toxicities including: growth retardation, weight gain, hypertension, hyperglycemia, hyperlipidemia, and Cushingoid features.

The objective of treatment of this patient population with Compound 1 is reduction (or normalization) of key hormonal outcome measures which could allow reduction of their GC replacement requirements which will improve clinical outcomes of concern, including growth velocity. Improvement of hormonal outcome measures in this population are also expected to delay premature puberty and bone maturation, ultimately leading to improvements in height in adolescents with CAH.

Outcome Measures
Primary Outcome Measures:
1. To evaluate the safety of Compound 1 in adolescent subjects with CAH.

Secondary Outcome Measures:
2. To evaluate the dose(s) of Compound 1 that cause changes in key pharmacodynamics biomarkers in blood in adolescent subjects with CAH.
3. To investigate the effect of Compound 1 on quality of life in adolescent subjects with CAH.
4. To determine the pharmacokinetics of Compound 1 in adolescent subjects with CAH.
5. To investigate potential relationships between pharmacodynamics and pharmacokinetics in adolescent subjects with CAH.

Exploratory
6. To explore the dose(s) of Compound 1 that cause changes in exploratory pharmacodynamics biomarkers in blood and urine in adolescent subjects with CAH.

Eligibility Criteria
Inclusion Criteria:
- Male and female subjects 12 to 17 years of age, inclusive
- Documented diagnosis of classic CAH due to 21-hydroxylase deficiency
- Elevated 17-OHP at screening
- On a stable regimen of glucocorticoid replacement for minimum of 30 days Exclusion Criteria:
  Clinically significant unstable medical condition, illness, or chronic disease
  Clinically significant psychiatric disorder.
  Clinically significant abnormal laboratory finding or assessment
  History of bilateral adrenalectomy or hypopituitarism
  Pregnant or nursing females
  Use of any other investigational drug within 30 days
  Unable to understand and comply with the study procedures, understand the risks, and/or unwilling to provide written informed consent.

Example 7: Phase 3 Clinical Studies

This is a 24-week, randomized, double-blind, placebo-controlled study of Compound 1 for the treatment of classic CAH. After screening, eligible patients will be enrolled into a 24-week treatment period followed by a 4-week safety follow-up period.

Subjects in the study will be randomized in a 1:1 ratio to either receive Compound 1 or a matching placebo for up to 24 weeks. Compound 1 or a placebo will be administered as an oral daily dose. Patients will return approximately monthly for study visits. A follow-up outpatient visit will occur 30 days after their last dose. It is initially planned that up to approximately 150 patients will be enrolled.

Consistent with the design of the Phase 2 study, the Phase 3 clinical study will seek to enroll patients with inadequately controlled CAH despite an existing glucocorticoid (GC) regimen (including any currently-available regimen: hydrocortisone, prednisone/prednisolone, and/or dexamethasone). In practice, CAH patients are typically treated with supraphysiologic doses of GCs which are both toxic and not effective in the majority of patients. GCs are associated with multiple well-described short- and long-term toxicities in adults including: excessive weight gain, hypertension, hyperglycemia, hyperlipidemia, and Cushingoid features.

Study Design:
  Study Type: Interventional
  Primary Purpose: Treatment
  Study Phase: Phase 3
  Interventional Study Model: Randomized Controlled Trial
  Allocation: Randomized
  Enrollment: 150 [Anticipated]
Outcome Measures
Primary Outcome Measures
  1. Evaluate efficacy of Compound 1 in reducing A4 and 17-OHP in patients with CAH.
Secondary Outcome Measures
  2. Evaluate efficacy of Compound 1 in patients with CAH in terms of changes in key hormones.
  3. Evaluate efficacy of Compound 1 in improving quality of life and/or mood in patients with CAH.
  4. Evaluate efficacy of Compound 1 in improving hyperandrogenic symptoms in patients with CAH.
  5. Evaluate efficacy of Compound 1 in improving metabolic parameters in patients with CAH.
  6. Evaluate safety of Compound 1 in patients with CAH.
Eligibility
  Minimum age: 16 Years
  Maximum Age:
  Sex: All
  Gender Based: No
  Accepts Healthy Volunteers: No
  Criteria: Inclusion Criteria
Inclusion Criteria:
  Male and female patients age 16 or older.
  Document diagnosis of classic CAH due to 21-hydroxylase deficiency
  Elevated 17-OHP
  On a stable glucocorticoid replacement regimen for a minimum of 30 days
Exclusion Criteria:
  Clinically significant unstable medical condition, illness, or chronic disease
  Clinically significant psychiatric disorder.
  Clinically significant abnormal laboratory finding or assessment
  History of bilateral adrenalectomy or hypopituitarism
  Pregnant or nursing females
  Use of any other investigational drug within 30 days
  Unable to understand and comply with the study procedures, understand the risks, and/or unwilling to provide written informed consent.

Example 8: Phase 3 OLE and Steroid Sparing Studies

Upon completion of the study described in Example 7, eligible patients will then be offered the opportunity to enroll into an open label extension study lasting up to 1 year. The open label study will allow all eligible patients to receive active study drug during their participation in the Phase 3 program. Patients will undergo study assessments every 1-3 months during the open label phase, and will be evaluated for long-term safety and efficacy (including both hormonal endpoints and long-term clinical outcome measures of concern in this population).

A further study may seek to enroll patients with inadequately controlled CAH despite an existing glucocorticoid (GC) regimen (including any currently-available regimen: hydrocortisone, prednisone/prednisolone, and/or dexamethasone). Such CAH patients are typically treated with supraphysiologic doses of GCs which are both toxic and not effective in the majority of patients. GCs are associated with multiple well-described short- and long-term toxicities in adults including: excessive weight gain, hypertension, hyperglycemia, hyperlipidemia, and Cushingoid features.

Following a period of treatment (for example 12 weeks) during the dose of GC will be kept stable, patients in this study will have their dose of GC progressively reduced from a supraphysiologic dose to a lower dose at or close to a dose equivalent to a physiologic dose of GC.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A method for treating congenital adrenal hyperplasia (CAH) in a human, comprising:
  administering to said human a therapeutically-effective amount of a $CRF_1$ receptor antagonist or a pharmaceutically acceptable salt thereof, wherein said human has received or has been previously determined to receive a first dose of a glucocorticoid, and administering to said human a second dose of a glucocorticoid, wherein said second dose of a glucocorticoid is reduced compared to said first dose of a glucocorticoid, wherein an androstenedione (A4) level in said human is reduced from baseline, or wherein an adrenocorticotropic hormone (ACTH) level in said human is reduced from baseline, or wherein a 17-hydroxyprogesterone (17-OHP) level in said human is reduced from baseline, wherein said CRF1 receptor antagonist or a pharmaceutically acceptable salt thereof is administered at a dose between about 50 mg/day and about 200 mg/day, and wherein said CRF1 receptor antagonist is stable for storage for a minimum of six months.

2. The method of claim 1, wherein said A4 level, said ACTH level, or said 17-OHP level in said human is reduced by at least 5% from baseline.

3. The method of claim 1, wherein said A4 level, said ACTH level, or said 17-OHP level in said human is reduced by at least 10% from baseline.

4. The method of claim 1, wherein said A4 level, said ACTH level, or said 17-OHP level in said human is reduced by at least 15% from baseline.

5. The method of claim 1, wherein said A4 level, said ACTH level, or said 17-OHP level in said human is reduced by at least 20% from baseline.

6. The method of claim 1, wherein said A4 level, said ACTH level, or said 17-OHP level in said human is reduced by at least 25% from baseline.

7. The method of claim 1, wherein said A4 level, said ACTH level, or said 17-OHP level in said human is reduced from baseline and is maintained at a reduced level post 24 hours.

8. The method of claim 1, wherein said A4 level, said ACTH level, or said 17-OHP level in said human is reduced from baseline and is maintained at a reduced level post 4 weeks.

9. The method of claim 1, wherein said A4 level, said ACTH level, or said 17-OHP level in said human is reduced from baseline and is maintained at a reduced level post 6 weeks.

10. The method of claim 1, wherein said administering of said first dose of said glucocorticoid is concurrently or sequentially within 2 hours of said administering of said therapeutically-effective amount of a $CRF_1$ receptor antagonist or a pharmaceutically acceptable salt thereof.

11. The method of claim 1, wherein said $CRF_1$ receptor antagonist or a pharmaceutically acceptable salt thereof is Compound 1:

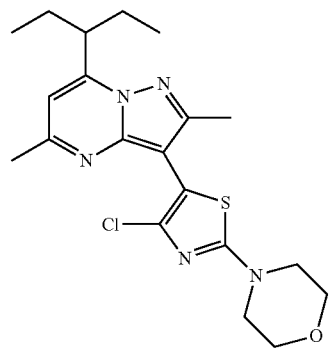 [SMILES: CCC(CC)c1cc(C)nc2c(-c3sc(N4CCOCC4)nc3Cl)c(C)nn12]

or a pharmaceutically acceptable salt thereof.

12. The method of claim 1, wherein said glucocorticoid is selected from beclomethasone, betamethasone, budesonide, cortisone, dexamethasone, hydrocortisone, methylprednisolone, prednisolone, prednisone, and triamcinolone.

13. The method of claim 1, wherein said glucocorticoid is hydrocortisone.

14. The method of claim 1, wherein said first dose of said glucocorticoid comprises a supraphysiologic amount of said glucocorticoid.

15. The method of claim 1, wherein said second dose of said glucocorticoid comprises a physiologic amount of said glucocorticoid.

16. The method of claim 1, wherein said CRF1 receptor antagonist or a pharmaceutically acceptable salt thereof is orally administered.

17. The method of claim 16, wherein said oral administration is once a day.

18. The method of claim 16, wherein said oral administration is twice a day.

19. The method of claim 1, wherein said first dose is a first daily dose and said second dose is a second daily dose.

20. The method of claim 1, wherein said second dose of said glucocorticoid is at least about 5%, at least about 10%, or at least about 20% lower than said first dose of said glucocorticoid.

21. The method of claim 1, wherein said CRF1 receptor antagonist is stable between about 25° C. and about 40° C.

* * * * *